US008183357B2

(12) United States Patent
Mather et al.

(10) Patent No.: US 8,183,357 B2
(45) Date of Patent: May 22, 2012

(54) ANTIBODIES THAT BIND TO EPHA2 AND METHODS OF USE THEREOF

(75) Inventors: Jennie P. Mather, Millbrae, CA (US); Penelope E. Roberts, Millbrae, CA (US)

(73) Assignee: MacroGenics, Inc., Rockville, MD (US)

( * ) Notice: Subject to any disclaimer, the term of this patent is extended or adjusted under 35 U.S.C. 154(b) by 376 days.

(21) Appl. No.: 12/627,335

(22) Filed: Nov. 30, 2009

(65) Prior Publication Data

US 2010/0086969 A1 Apr. 8, 2010

Related U.S. Application Data

(62) Division of application No. 12/495,218, filed on Jun. 30, 2009, now Pat. No. 7,776,328, and a division of application No. 11/349,327, filed on Feb. 6, 2006, now Pat. No. 7,569,672.

(60) Provisional application No. 60/650,047, filed on Feb. 4, 2005.

(51) Int. Cl.
*C07H 21/04* (2006.01)

(52) U.S. Cl. .................. 536/23.53; 435/451

(58) Field of Classification Search .......... None
See application file for complete search history.

(56) References Cited

U.S. PATENT DOCUMENTS

| 4,816,567 | A | 3/1989 | Cabilly et al. |
| 5,552,391 | A | 9/1996 | Coutts et al. |
| 5,565,332 | A | 10/1996 | Hoogenboom et al. |
| 5,580,717 | A | 12/1996 | Dower et al. |
| 5,656,444 | A | 8/1997 | Webb et al. |
| 5,733,743 | A | 3/1998 | Johnson et al. |
| 5,807,715 | A | 9/1998 | Morrison et al. |
| 5,824,303 | A | 10/1998 | Bartley et al. |
| 5,866,692 | A | 2/1999 | Shitara et al. |
| 5,997,867 | A | 12/1999 | Waldmann et al. |
| 6,054,297 | A | 4/2000 | Carter et al. |
| 6,054,561 | A | 4/2000 | Ring |
| 6,180,377 | B1 | 1/2001 | Morgan et al. |
| 6,210,671 | B1 | 4/2001 | Co |
| 6,265,150 | B1 | 7/2001 | Terstappen et al. |
| 6,331,415 | B1 | 12/2001 | Cabilly et al. |
| 6,350,861 | B1 | 2/2002 | Co et al. |
| 6,441,163 | B1 | 8/2002 | Chari et al. |
| 6,541,225 | B1 | 4/2003 | Li |
| 6,927,203 | B1 | 8/2005 | Kinch et al. |
| 7,569,672 | B2 | 8/2009 | Mather et al. |
| 2006/0034856 | A1 | 2/2006 | Kosmatopoulos et al. |
| 2009/0263391 | A1 | 10/2009 | Mather et al. |

FOREIGN PATENT DOCUMENTS

| EP | 0519596 | 12/1992 |
| WO | WO 00/37503 | 6/2000 |
| WO | WO 01/12172 | 2/2001 |
| WO | WO 01/12840 | 2/2001 |
| WO | WO 01/27160 | 4/2001 |
| WO | WO 01/43869 | 6/2001 |
| WO | WO 03/091383 | 11/2003 |
| WO | WO 03/094859 | 11/2003 |
| WO | WO 2004/014292 | 2/2004 |

OTHER PUBLICATIONS

Aruffo, A. et al. (Dec. 1987). "Molecular Cloning of a CD28 cDNA by a High-Efficiency COS Cell Expression System," Proc. Natl. Acad. Sci. USA 84:8573-8577.
Bartley, T.D. et al. (Apr. 7, 1994). "B61 is a Ligand for the ECK Receptor Protein-Tyrosine Kinase," Nature 368:558-560.
Bird, R.E. et al. (Oct. 21, 1988). "Single-Chain Antigen-Binding Proteins," Science 242:423-426.
Brown, B.A. et al. (Jul. 1, 1987). "Tumor-Specific Genetically Engineered Murine/Human Chimeric Monoclonal Antibody," Cancer Res. 47:3577-3583.
Carles-Kinch, K. et al. (May 15, 2002). "Antibody Targeting of the EphA2 Tyrosine Kinase Inhibits Malignant Cell Behavior," Cancer Res. 62:2840-2847.
Daugherty, B.L. et al. (1991). "Polymerase Chain Reaction Facilitates the Cloning, CDR-Grafting, and Rapid Expression of a Murine Monoclonal Antibody Directed Against the CD18 Component of Leukocyte Integrins," Nucl. Acids Res. 19(9):2471-2476.
Dillman, R.O. et al. (Nov. 1, 1988). "Superiority of an Acid-Labile Daunorubicin—Monoclonal Antibody Immunoconjugate Compared to Free Drug," Cancer Res. 48:6097-6102.
Duxbury, M.S. et al. (2004). "Ligation of EphA2 by Ephrin A1-Fc Inhibits Pancreatic Adenocarcinoma Cellular Invasiveness," Biochem. Biophys. Res. Commun. 320: 1096-1102.
Easty, D.J. et al. (1995). "Abnormal Protein Tyrosine Kinase Gene Expression During Melanoma Prouresslon and Metastasis," Int. J. Cancer 60:129-136.
Gennaro, A.R. ed. (2000). Remington: The Science and Practice of Pharmacy 20th Edition, Lippincott Williams and Wilkins, pp. xiv-xv (Table of Contents Only).
Goldenberg, D.M. ed. (1995). Cancer Therapy With Radiolabeled Antibodies, CRC Press: Boca Raton, FL, two pages. (Table of Contents Only).
Jones, P.T. et al. (May 29, 1986). "Replacing the Complementarity-Determining Regions in a Human Antibody with Those from a Mouse," Nature 321:522-525.
Kane, S. et al. (Jun. 21, 2002). "A Method to Identify Serine Kinase Substrates," J. Biol. Chem. 277(25):22115-22118.
Kinch, M.S. et al. (2003). "Overexpression and Functional Alterations of the EphA2 Tyrosine Kinase in Cancer," Clinical & Experimental Metastasis 20(1):59-68.
Kohler, G. et al. (Aug. 7, 1975). "Continuous Cultures of Fused Cells Secreting Antibody of Predefined Specificity," Nature 256:495-497.
Lindberg, R.A. et al. (Dec. 1990). "cDNA Cloning and Characterization of eck, an Epithelial Cell Receptor Protein-Tyrosine Kinase in the eph/elk Family of Protein Kinases," Mol. Cell. Biol. 10(12):6316-6324.

(Continued)

Primary Examiner — Misook Yu
Assistant Examiner — Mark Halvorson
(74) Attorney, Agent, or Firm — William C. Schrot; Jeffrey I. Auerbach; The Auerbach Law Firm, LLC

(57) ABSTRACT

Provided herein is disclosure about the development and characterization of an antibody that binds to antigen EphA2 which is present on a variety of human cancers from breast, lung, prostate, and colons. Methods of diagnosing and treating various cancers by using such antibodies directed against this antigen are also disclosed.

36 Claims, 1 Drawing Sheet

OTHER PUBLICATIONS

LoBuglio, A.F. et al. (Jun. 1989). "Mouse/Human Chimeric Monoclonal Antibody in Man: Kinetics and Immune Response," Proc. Natl. Acad. Sci. USA 86:4420-4224.

Mahato, R.I. et al. (1997). "Cationic Lipid-Based Gene Delivery Systems: Pharmaceutical Perspectives," Pharm. Res. 14(7):853-859.

Mangham, D.C. et al. (1999). "A Novel Immunohistochemical Detection System Using Mirror Image Complementary Antibodies (MICA)," Histopathology 35(2):129-133.

Riechmann, L. et al. (Mar. 24, 1988). "Reshaping Human Antibodies for Therapy," Nature 332:323-327.

Rosenberg, I.M. et al. (1997). "Epithelial Cell Kinase-B61: An Autocrine Loop Modulating Intestinal Epithelial Migration and Barrier Function," Am. J. Physiol. 273:G824-G832.

Shaw, D.R. et al. (Jun. 15, 1987). "Characterization of a Mouse/Human Chimeric Monoclonal Antibody (17-1A) to a Colon Cancer Tumor-Associated Antigen," J. Immunology 138(12):4534-4538.

Shen, W-C. et al. (Oct. 15, 1981). "Cis-Aconityl Spacer Between Daunomycin and Macromolecular Carriers: A Model of pH-Sensitive Linkage Releasing Drug from a Lysosomotrooic Conjugate," Biochem. Biophys. Res. Commun. 102(3):1048-1054.

Stephan, J-P. et al. (1999). "Distribution and Function of the Adhesion Molecule BEN During Rat Development," Dev. Biol. 212:264-277.

Stephan, J-P. et al. (1999). "Selective Cloning of Cell Surface Proteins Involved in Organ Development: Epithelial Glycoprotein Is Involved in Normal Epithelial Differentiation," Endocrinology 140(12):5841-5854.

Sulman, E.P. et al. (Mar. 1, 1997). "ECK, A Human EPH-Related Gene, Maps to 1 p36.1, a Common Region of Alteration in Human Cancers," Genomics 40(2):371-374.

Trouet, A. et al. (Jan. 1982). "A Covalent Linkage Between Daunorubicin and Proteins that is Stable in Serum and Reversible by Lysosomal Hydrolases, as Required for a Lysosomotropic Drug-Carrier Conjugate: in vitro and in vivo Studies," Proc. Natl. Acad. Sci. USA 79(1):626-629.

Verhoeyen, M. et al. (1988). "Reshaping Human Antibodies: Grafting an Antilysozyme Activity," Science 239:1534-1536.

Walker-Daniels, J. et al. (1999). "Overexpression of the EphA2 Tyrosine Kinase in Prostate Cancer," Prostate 41:275-280.

Walker-Daniels, J. et al. (Nov. 2002). "c-Cbl-Dependent EphA2 Protein Degradation Is Induced by Liagnd Binding," Mol. Cancer Res. 1:79-87.

Weiner, L.M. et al. (2001). "Therapeutic Monoclonal Antibodies: General Principles," Chapter 20, Section 5, in Cancer: Principles and Practice of Oncology, Sixth Edition, Freeman, S. et al. eds, Lippincott Williams & Wilkins, pp. 495-508.

Wheatley, S.P. et al. (1998). "Indirect Immunofluorescence Microscopy in Cultured Cells" Chapter 18, In Animal Cell Culture Methods: Methods in Cell Biology, Mather, J.P. et al. eds., Academic Press, vol. 57, pp. 313-332.

Winter, G. et al. (Jan. 24, 1991). "Man-Made Antibodies," Nature 349:293-299.

Winter, G. et al. (1994). "Making Antibodies by Phage Display Technology," Annu. Rev. Immunol. 12:433-455.

Woodruff, T.K. (1998). "Cellular Localization of mRNA and Protein: In Situ Hybridization Histochemistry and in Situ Ligand Binding," Chapter 19 In Animal Cell Culture Methods: Methods in Cell Biology, Mather, J.P. et al. eds., Academic Press, vol. 57, pp. 333-351.

Wu, X. et al. (May 25, 2000) "ATM Phosphorylation of Nijmegen Breakage Syndrome Protein is Required in a DNA Damage Response," Nature 405:477-482.

Yang, H.M. et al. (Sep. 21, 1988). "Pharmacokinetics and Mechanism of Action of a Doxorubicin-Monoclonal Antibody 9.2.27 Conjugate Directed to a Human Melanoma Proteoglycan," J. Natl. Canc. Inst. 80(14):1154-1159.

Zantek, N.D. et al. (Sep. 1999). "E-Cadherin Regulates the Function of the EphA2 Receptor Tyrosine Kinase," Cell Growth and Differ. 10:629-638.

Zantek, N.D. et al. (Nov. 2001). "MCF-10A-NeoST: A New Cell System for Studying Cell-ECM and Cell-Cell Interactions in Breast Cancer," Clin. Cancer Res. 7:3640-3648.

Zelniski, D.P. et al. (Mar. 1, 2001). "EphA2 Overexpression Causes Tumorigenesis of Mammary Epithelial Cells," Cancer Res. 61:2301-2306.

Supplementary European Search Report issued on May 2, 2008 for EP application 06734397.0, filed on Feb. 6, 2006, 3 pages.

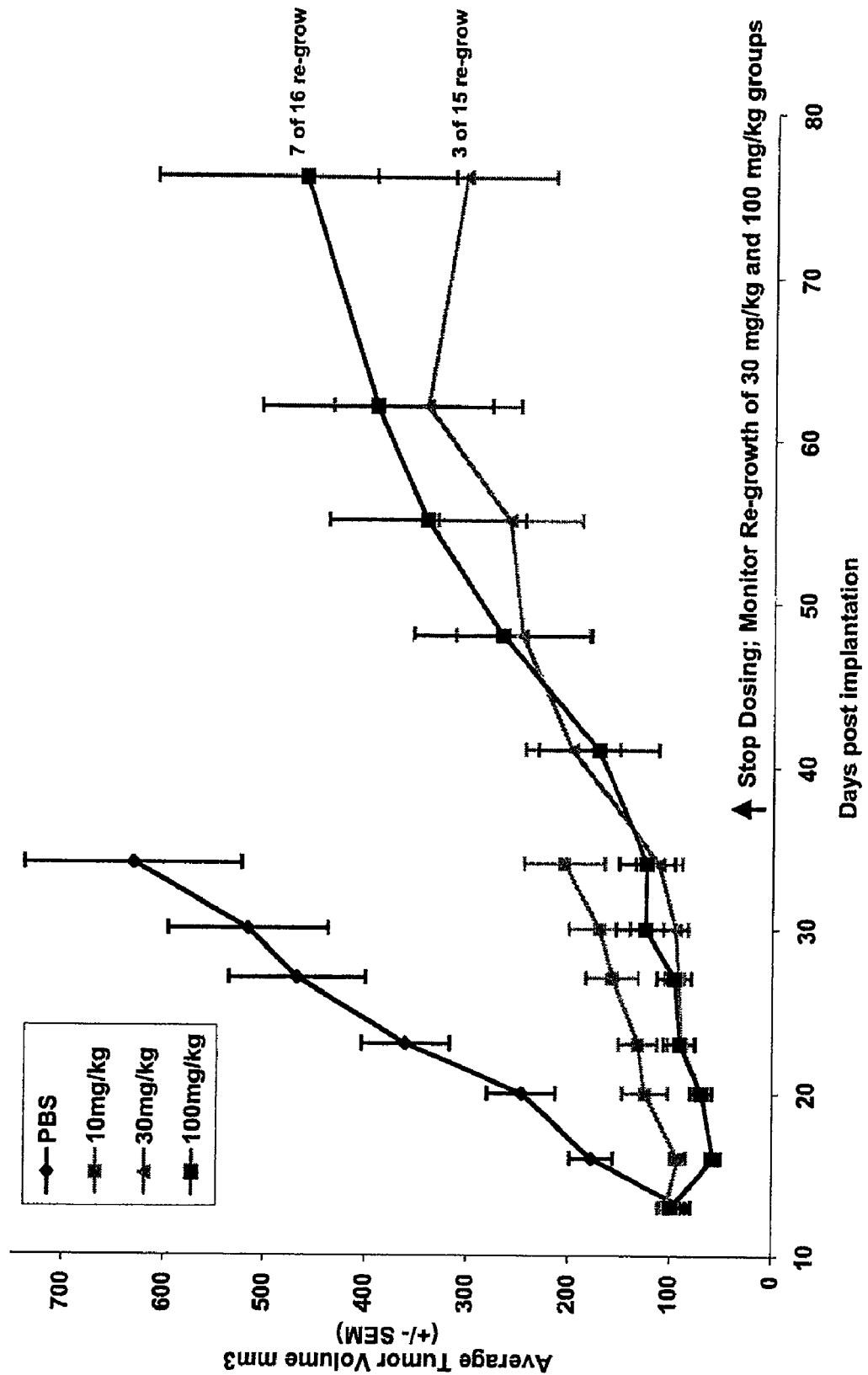

ANTIBODIES THAT BIND TO EPHA2 AND METHODS OF USE THEREOF

TECHNICAL FIELD

This invention is in the fields of biology and immunotherapy. More specifically, it concerns the discovery of a family of antibodies that bind to EphA2. The invention further provides the diagnosis and/or treatment of a variety of human diseases and cancers associated with EphA2 using anti-EphA2 family antibodies.

BACKGROUND OF THE INVENTION

In addition to their known uses in diagnostics, antibodies have been shown to be useful as therapeutic agents. For example, immunotherapy, or the use of antibodies for therapeutic purposes has been used in recent years to treat cancer. Passive immunotherapy involves the use of monoclonal antibodies in cancer treatments. See for example, *Cancer: Principles and Practice of Oncology*, 6th Edition (2001) Chapt. 20 pp. 495-508. These antibodies can have inherent therapeutic biological activity both by direct inhibition of tumor cell growth or survival and by their ability to recruit the natural cell killing activity of the body's immune system. These agents can be administered alone or in conjunction with radiation or chemotherapeutic agents. Rituximab and Trastuzumab, approved for treatment of non-Hodgkin's lymphoma and breast cancer, respectively, are two examples of such therapeutics. Alternatively, antibodies can be used to make antibody conjugates where the antibody is linked to a toxic agent and directs that agent to the tumor by specifically binding to the tumor. Gemtuzumab ozogamicin is an example of an approved antibody conjugate used for the treatment of leukemia. Monoclonal antibodies that bind to cancer cells and have potential uses for diagnosis and therapy have been disclosed in publications. See, for example, the following patent applications which disclose, inter alfa, some molecular weights of target proteins: U.S. Pat. No. 6,054,561 (200 KD c-erbB-2 (Her2), and other unknown antigens 40-200 KD in size) and U.S. Pat. No. 5,656,444 (50 KD and 55 KD, oncofetal protein). Example of antibodies in clinical trials and/or approved for treatment of solid tumors include: Trastuzumab (antigen: 180 kD, HER2/neu), Edrecolomab (antigen: 40-50 kD, Ep-CAM), Anti-human milk fat globules (HMFG1) (antigen >200 kD, HMW Mucin), Cetuximab (antigens: 150 kD and 170 kD, EGF receptor), Alemtuzumab (antigen: 21-28 kD, CD52), and Rituximab (antigen: 35 kD, CD20).

The antigen targets of trastuzumab (Her-2 receptor), which is used to treat breast cancer, and cetuximab (EGF receptor), which is in clinical trials for the treatment of several cancers, are present at some detectable level on a large number of normal human adult tissues including skin, colon, lung, ovary, liver, and pancreas. The margin of safety in using these therapeutics is possibly provided by the difference in the level of expression or in access of or activity of the antibody at these sites.

Another type of immunotherapy is active immunotherapy, or vaccination, with an antigen present on a specific cancer(s) or a DNA construct that directs the expression of the antigen, which then evokes the immune response in the individual, i.e., to induce the individual to actively produce antibodies against their own cancer. Active immunization has not been used as often as passive immunotherapy or immunotoxins.

Several models of disease (including cancer) progression have been suggested. Theories range from causation by a single infective/transforming event to the evolution of an increasingly "disease-like" or 'cancer-like' tissue type leading ultimately to one with fully pathogenic or malignant capability. Some argue that with cancer, for example, a single mutational event is sufficient to cause malignancy, while others argue that subsequent alterations are also necessary. Some others have suggested that increasing mutational load and tumor grade are necessary for both initiation as well as progression of neoplasia via a continuum of mutation-selection events at the cellular level. Some cancer targets are found only in tumor tissues, while others are present in normal tissues and are up-regulated and/or over-expressed in tumor tissues. In such situations, some researchers have suggested that the over-expression is linked to the acquisition of malignancy, while others suggest that the over-expression is merely a marker of a trend along a path to an increasing disease state.

One aspect required for the ideal diagnostic and/or therapeutic antibody is the discovery and characterization of an antigen that is associated with a variety of cancers. There are few antigens that are expressed on a number of types of cancer (e.g., "pan-cancer" antigen) that have limited expression on non-cancerous cells. The isolation and purification of such an antigen would be useful for making antibodies (e.g., diagnostic or therapeutic) targeting the antigen. An antibody binding to the "pan-cancer" antigen could be able to target a variety of cancers found in different tissues in contrast to an antibody against an antigen associated with only one specific type of cancer. The antigen would also be useful for drug discovery (e.g., small molecules) and for further characterization of cellular regulation, growth, and differentiation.

What is needed are novel targets on the surface of diseased and/or cancer cells that may be used to treat such diseases and/or cancers with antibodies and other agents which specifically recognize the cell surface targets. There exists a further need, based on the discoveries disclosed herein, for novel antibodies and other agents which specifically recognize targets on the surface of cells that can modulate, either by reducing or enhancing, the disease-promoting activities of EphA2.

EphA2, previously known as ECK, is a 130 kD transmembrane receptor tyrosine kinase that is expressed on adult epithelial cells. See Lindberg, et al. (1990) *Mol. Cell. Biol.* 10: 6316-6324. EphA2 is one member of the Eph family of receptor tyrosine kinases, which are unique in that they recognize ligands, known as ephrins, which are anchored to the membrane of adjacent cells. See Bartley, et al. (1994) *Nature* 368: 558-560. The sequence of the human receptor EphA2 is known in the literature. It encompasses an extracellular domain of 534 amino acids, a transmembrane domain of 24 amino acids, and a cytoplasmic domain of 418 amino acids that contains the tyrosine kinase domain.

EphA2 is over-expressed in a large number of cancer cells, for example, in breast, prostate, lung, and colon carcinomas, and in aggressive melanomas, but reportedly is not over-expressed in non-cancerous lesions of these same tissues. See, for example, Rosenberg, et al. (1997) *Am. J. Physiol.* 273: G824-G832; Easty, et al., (1995) *Int. J. Cancer* 60: 129-136; Walker-Daniels, et al. (1999) Prostate 41: 275-280; Zantek et al. (1999) Cell Growth & Differ. 10: 629-638; Zantek et al. (2001) *Clin. Cancer Res.* 7: 3640-3648; Zelniski et al. (2001) *Cancer Res.* 61: 2301-2306; WO 01/121172; and WO 01/12840. Moreover, cells that have been transformed to over-express EphA2 demonstrate malignant growth and ligand binding, which causes EphA2 to be internalized and degraded, and reverses the oncogenic effect of EphA2 over-expression. See Zelniski et al. (2001) *Cancer Res.* 61: 2301-2306; and Walker-Daniels, et al. (2002) *Mol. Cancer Res.* 1: 79-87.

Using EphA2 as a therapeutic target has been proposed by others in the art. One author suggested using EphA2 ligands such as an Ephrin A1 fusion to human immunoglobulin G. Exposure of cells expressing EphA2 to the Ephrin A1-Fc fusion protein resulted in a down-regulation of EphA2 expression. See Duxbury, et al. (2004) *BBRC* 320:1096-1102.

Antibodies to eck/EphA2 are known, see e.g., Lindberg, et al. (1990) *Mol. Cell. Biol.* 10: 6316-6324. The use of antibody-based targeting using anti-EphA2 antibodies has been described by others, see e.g., Charles-Kinch et al. (2002) *Cancer Res.* 62:2840-2847, which describes using extracellular domain of EphA2 fused to human immunoglobulin to generated monoclonal antibodies against EphA2. Treatment of cancer cells with these anti-EphA2 monoclonal antibodies resulted in morphological changes and inhibition of cell growth on soft agar.

Antibodies to EphA2 have been made and proposed to be useful in the treatment of cancer (see e. g., U.S. Pat. No. 6,927,203; International Patent Publication Nos. WO01/12840 and WO01/12172; U.S. Provisional Patent Application Nos. 60/379,322 and 60/379,368; U.S. Pat. No. 5,824,303). WO2003US15044 describes methods comprising the administration of an effective amount of an antibody that binds to EphA2 and agonizes EphA2, thereby increasing EphA2 phosphorylation and decreasing EphA2 levels. In other embodiments, that application describes the administration of an effective amount of an antibody that binds to EphA2 and inhibits cancer cell colony formation in soft agar, inhibits tubular network formation in three-dimensional basement membrane or extracellular matrix preparation, preferentially binds to an EphA2 epitope that is exposed on cancer cells but not non-cancer cells, and/or has a low Koff, thereby, inhibiting tumor cell growth and metastasis. U.S. Pat. No. 6,927,203 describes antibodies that impede proliferation of tumor cells using an antibody that increases the phosphotyrosine content of EphA2.

PCT patent application WO 200391383 describes peptides derived from EphA2 and their use in anti-tumor immunotherapy. It describes peptide vaccination or immunotherapy based on an EphA2 epitope that may be used to induce or mimic a cytotoxic T lymphocyte cell response to tumor cells that over-express EphA2.

While EphA2 antibodies are known, there remains a need for particular anti-EphA2 antibodies that are extremely effective in inhibiting tumor cell growth, beyond the level of effectiveness shown by the EphA2 antibodies shown in the prior art.

All references, publications, and patent applications disclosed herein are hereby incorporated by reference in their entirety.

SUMMARY OF THE INVENTION

The invention disclosed herein concerns antibodies that bind to an antigen, EphA2, which is expressed on a variety of human cancers. Accordingly, in one aspect, the invention is a family of antibodies, or an antibody or a polypeptide (which may or may not be an antibody) that binds preferentially to the antigen EphA2. The antibodies claimed in the present invention are surprisingly and very effective in inhibiting tumor cell growth, beyond the level of effectiveness shown by the EphA2 antibodies shown in the prior art. Some of these antibodies are referred to herein as LUCA19, SPL1, LUCA40, or SG5. In aspects of this invention, certain antibodies have been discovered that have the ability to impede proliferation of tumor cells while not increasing the phosphotyrosine content of EphA2.

In another aspect, the invention is a monoclonal antibody anti-EphA2 that is produced by any one of the following host cell lines: PTA-5070 deposited Mar. 20, 2003 at the American Type Culture Collection, PTA-6056 deposited Jun. 8, 2004 at the American Type Culture Collection, PTA-6059 deposited Jun. 8, 2004 at the American Type Culture Collection, and an SG5-producing host cell line (SG.3.15.B4.1F9) was deposited at the American Type Culture Collection on Feb. 2, 2006.

In another aspect, the invention is an antibody or a polypeptide (which may or may not be an antibody) that competitively inhibits specific binding of the anti-EphA2 antibody to EphA2. In another aspect, the invention is an antibody or a polypeptide (which may or may not be an antibody) that binds preferentially to the same epitope on EphA2 as LUCA19, SPL1, SG5 or LUCA40 binds preferentially.

In another aspect, the invention is an antibody comprising a fragment or a region of the anti-EphA2 antibody. In one embodiment, the fragment is a light chain of the anti-EphA2 antibody. In another embodiment, the fragment is a heavy chain of the anti-EphA2 antibody. In yet another embodiment, the fragment contains one or more variable regions from a light chain and/or a heavy chain of the anti-EphA2 antibody. In yet another embodiment, the fragment contains one or more complementarity determining regions (CDRs) from a light chain and/or a heavy chain of the anti-EphA2 antibody.

In another aspect, the invention provides polypeptides (which may or may not be antibodies) comprising any of the following: a) one or more CDRs; b) three CDRs from the light chain; c) three CDRs from the heavy chain; d) three CDRs from the light chain and three CDRs from the heavy chain; e) the light chain variable region; f) the heavy chain variable region of the anti-EphA2 antibody.

In another aspect, the invention is a humanized antibody derived from LUCA19, SPL1, SG5 or LUCA40. In some embodiments, the humanized antibody comprises one or more CDRs of the anti-EphA2 antibody. In another aspect, the invention provides a humanized antibody that binds to the same epitope(s) as anti-EphA2 antibody. Generally, a humanized antibody of the invention comprises one or more (one, two, three, four, five, six) CDRs that are the same and/or derived from the CDR(s) of anti-EphA2 antibody. In other aspect, the invention provides a human antibody that binds to the same epitope(s) on EphA2 as anti-EphA2 antibody.

In anther aspect, the invention is a chimeric antibody comprising variable regions derived from variable regions of a heavy chain and a light chain of anti-EphA2 antibody and constant regions derived from constant regions of a heavy chain and a light chain of a human antibody.

In yet another aspect, the invention is a host cell (ATCC No. PTA-5070, PTA-6056, PTA-6059, or SG.3.15.B4.1F9 (ATCC No. PTA-XXXX)) or progeny thereof which produces monoclonal anti-EphA2 antibody.

In another aspect, the invention is an isolated polynucleotide that encodes for anti-EphA2 antibody that is produced by a host cell with a deposit number of ATCC No. PTA-5070, PTA-6056, or PTA-6059 or host cell SG.3.15.B4.1F9 (ATCC No. PTA-XXXX) or progeny thereof. In another aspect, the invention provides polynucleotides encoding any of the antibodies (including antibody fragments) as well as any other polypeptides described herein.

In another aspect, the invention is a complex of EphA2 bound by any of the antibody or polypeptides described herein. In some embodiments, the EphA2 is present on melanomas, breast, colon, lung, or prostate cancer cells. In some embodiments, the invention is a complex of EphA2 bound by anti-EphA2 antibody or an antibody that binds preferentially to the epitope that anti-EphA2 antibody binds preferentially. In one embodiment, anti-EphA2 antibody or any antibody that binds preferentially to the epitope that anti-EphA2 antibody binds preferentially is linked to a therapeutic agent (such as a toxin).

In another aspect, the invention is a complex of a cancer cell expressing EphA2 bound by any of the antibody or polypeptides described herein. In some embodiments, the cancer cell is melanomas, breast, colon, lung, or prostate cancer cell. In some embodiments, the antibody is SPL1, LUCA19, SG5 or LUCA40 or any antibody that binds preferentially to an epitope that any of these anti-EphA2 antibodies bind preferentially. In some embodiments, SPL1, LUCA19, SG5 or LUCA40 antibody or any antibody that binds preferentially to an epitope that any of these anti-EphA2 antibodies bind preferentially is linked to a therapeutic agent (such as a toxin).

In another aspect, the invention is a complex of an epitope on EphA2 that SPL1, LUCA19, SG5 or LUCA40 preferentially binds, which is in turn bound by any of the antibody or polypeptides described herein. In some embodiments, the epitope is on melanomas, breast, colon, lung, or prostate cancer cell. In some embodiments, the antibody is SPL1, LUCA19, SG5 or LUCA40 or any antibody that binds preferentially to an epitope that any of these anti-EphA2 antibodies bind preferentially. In some embodiments, SPL1, LUCA19, SG5 or LUCA40 or any antibody that binds preferentially to an epitope that any of these anti-EphA2 antibodies bind preferentially is linked to a therapeutic agent (such as a toxin).

In another aspect, the invention is a pharmaceutical composition comprising any of the polypeptides (including any of the antibodies such as anti-EphA2 antibody) or polynucleotides described herein, such as pharmaceutical compositions comprising the anti-EphA2 antibody, the anti-EphA2 antibody linked to a therapeutic agent, an antibody comprising a fragment of the anti-EphA2 antibody, a humanized antibody of the anti-EphA2 antibody, a chimeric antibody comprising variable regions derived from variable regions of the anti-EphA2 antibody and constant regions derived from constant regions of a human antibody, or a human antibody with one or more properties of the anti-EphA2 antibody, and a pharmaceutically acceptable excipient.

In yet another aspect, the invention is a method of generating monoclonal antibody anti-EphA2 reactive with diseased and/or cancerous cells comprising the steps of: (a) immunizing a host mammal with an immunogen; (b) obtaining lymphocytes from the mammal; (c) fusing lymphocytes (b) with a myeloma cell line to produce a hybridoma; (d) culturing the hybridoma of (c) to produce monoclonal antibodies; and (e) screening the antibodies to select only those antibodies which bind to diseased and/or cancerous cells or cell lines but do not bind to non-cancerous or normal cells or cell lines, or bind to normal cells at a lower level or in a different fashion.

In another aspect, the invention is a method of generating an anti-EphA2 family antibody comprising culturing a host cell encoding such antibody or progeny thereof under conditions that allow production of the antibody, and purifying the anti-EphA2 antibody.

In another aspect, the invention is a method of generating an anti-EphA2 family antibody comprising culturing a host cell or progeny thereof under conditions that allow production of the antibody, and purifying the anti-EPHA2 antibody.

In another aspect, the invention provides methods of generating any of the antibodies (or polypeptides) described herein by expressing one or more polynucleotides encoding the antibody (which may be separately expressed as a single light or heavy chain, or both a light and a heavy chain are expressed from one vector) in a suitable cell, generally followed by recovering and/or isolating the antibody or polypeptides of interest.

In another aspect, the invention is an anti-EphA2 antibody or a polypeptide (which may or may not be an antibody) that competitively inhibits preferential binding of an anti-EphA2 antibody to EphA2. In some embodiments, the invention is an antibody or a polypeptide (which may or may not be an antibody) that binds preferentially to the same or different epitopes on EphA2 as other anti-EphA2 antibodies.

In yet another aspect, the invention is a composition comprising EphA2 bound by an antibody specific for an epitope of EphA2. In one embodiment, the antibody is anti-EphA2. In other embodiments, two or more anti-EphA2 antibodies are administered, with such antibodies mapping to two or more different epitopes of EphA2. In some embodiments, the anti-EphA2 antibody is linked to a therapeutic agent or a detectable label.

In another aspect, the invention is an antibody comprising a fragment or a region of an anti-EphA2 antibody. In one embodiment, the fragment is a light chain of the antibody. In another embodiment, the fragment is a heavy chain of the antibody. In yet another embodiment, the fragment contains one or more variable regions from a light chain and/or a heavy chain of the antibody. In yet another embodiment, the fragment contains one or more complementarity determining regions (CDRs) from a light chain and/or a heavy chain of the antibody.

In another aspect, the invention provides polypeptides (which may or may not be antibodies) comprising any of the following: a) one or more CDRs (or fragments thereof) from the light or heavy chain; b) three CDRs from the light chain; c) three CDRs from the heavy chain; d) three CDRs from the light chain and three CDRs from the heavy chain; e) the light chain variable region; f) the heavy chain variable region of the anti-EphA2 antibody.

In another aspect, the invention is a humanized antibody. In some embodiments, the humanized antibody comprises one or more CDRs of a non-human anti-EphA2 antibody. In some embodiments, the humanized antibody binds to the same or different epitope(s) as other anti-EphA2 antibodies. Generally, a humanized antibody of the invention comprises one or more (one, two, three, four, five, six, or fragments thereof) CDRs which are the same and/or derived from the CDR(s) of the original non-human anti-EphA2 antibody. In some embodiments, the human antibody binds to the same or different epitope(s) as other anti-EphA2 antibodies. In anther aspect, the invention is a chimeric antibody comprising variable regions derived from variable regions of a heavy chain and a light chain of a non-human anti-EphA2 antibody and constant regions derived from constant regions of a heavy chain and a light chain of a human antibody.

In another aspect, the invention is an isolated polynucleotide that encodes any one of antibodies LUCA19, LUCA40, SPL1 or SG5 that is produced by a host cell with a deposit number of ATCC No. PTA-5070, PTA-6056, or PTA-6059, respectively, and host cell SG.3.15.B4.1F9 (ATCC No. PTA-7356) or progeny thereof. This invention encompasses antibody polypeptides having the inherent binding or biological activities of any of the above-specified antibodies. In another aspect, the invention provides polynucleotides encoding any of the antibodies (including antibody fragments) as well as any other polypeptides described herein.

In another aspect, the invention is a pharmaceutical composition comprising any of the polypeptides (including any of the antibodies described herein) or polynucleotides described herein, such as pharmaceutical compositions comprising an anti-EphA2 antibody linked to a chemotherapeutic agent, an antibody comprising a fragment of an anti-EphA2 antibody, a humanized antibody of a non-human anti-EphA2 antibody, a chimeric antibody comprising variable regions derived from variable regions of a non-human anti-EphA2 antibody and constant regions derived from constant regions of a human antibody, or a human antibody with one or more properties of a non-human anti-EphA2 antibody, or any of the anti-EphA2 antibody described herein linked to a chemotherapeutic agent (such as a radioactive moiety), and a pharmaceutically acceptable excipient.

In one aspect, the invention is a composition comprising an anti-EphA2 antibody bound to EphA2 present on a diseased or cancerous cell. In preferred embodiments, the cancer cell is selected from the group consisting of ovarian, lung, prostate, pancreatic, colon, and breast cancer cells. In some embodiments, the cancer cell is isolated. In some embodiments, the cancer cell is in a biological sample. Generally, the biological sample is from an individual, such as a human.

In another aspect, the invention is a method of diagnosing disease in an individual by detecting EphA2 on cells from the individual, particularly diseases or disorders associated with inflammatory or autoimmune responses in individuals. In other aspects of the invention, methods are provided for modulating inflammatory or autoimmune responses in individuals. Diseases and conditions resulting from inflammation and autoimmune disorders that may be subject to treatment using the compositions and methods of the invention include, by way of illustration and not of limitation, multiple sclerosis, meningitis, encephalitis, stroke, other cerebral traumas, inflammatory bowel disease including ulcerative colitis and Crohn's disease, myasthenia gravis, lupus, rheumatoid arthritis, asthma, acute juvenile onset diabetes, AIDS dementia, atherosclerosis, nephritis, retinitis, atopic dermatitis, psoriasis, myocardial ischemia and acute leukocyte-mediated lung injury.

Still other indications for therapeutic use of antibodies and other therapeutic agents of the invention include administration to individuals at risk of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue.

In another aspect, the invention is a method for diagnosing whether an individual has cancer, comprising determining whether there is expression of EphA2 on selected cells from the individual, wherein the expression of EphA2 on said cells is indicative of said cancer. In some embodiments, the expression of EphA2 is determined using an anti-EphA2 antibody. In some embodiments, the method involves detecting the level of EphA2 expression from cells. The term "detection" as used herein includes qualitative and/or quantitative detection (measuring levels) with or without reference to a control.

In yet another aspect, the invention is a method of diagnosing cancer in an individual by detecting EphA2 on or released from cells from the individual, wherein the cancer is selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, dhordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma, etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In another aspect, the invention is a method for aiding diagnosis of cancer (such as but not limited to ovarian, lung, prostate, pancreatic, colon, or breast cancer) in an individual comprising determining the expression of EphA2 in a biological sample from the individual. In some embodiments, the expression of EphA2 is determined using an anti-EphA2 antibody. In some embodiments, the anti-EphA2 antibody is a family member specifically named herein. In some embodiments, the method is detecting the level of EphA2 expression from cells.

In yet another aspect, the invention is a method of treating cancer by administering an effective amount of an antibody that binds to EphA2 sufficient to reduce growth of cancerous cells. In some embodiments, the antibody is an anti-EphA2 antibody. In certain embodiments, the cancerous cells are selected from the group including but not limited to adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, dhordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large carcinoma, etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma). In certain preferred embodiments, the cancerous cells are selected from the group of solid tumors including but not limited to breast cancer, colon cancer, prostate cancer, lung cancer, sarcoma, renal metastatic cancer, thyroid metastatic cancer, and clear cell carcinoma.

In yet another aspect, the invention is a method of delaying development of metastasis in an individual having cancer comprising administering an effective amount of at least one of a family of antibodies that bind specifically to EphA2. In one embodiment, the antibody is an anti-EphA2 antibody. In another aspect, the invention is a method of inhibiting growth and/or proliferation of cancer cells in vitro or in an individual comprising administering an effective amount of a composition comprising an anti-EphA2 antibody associated with (including linked to) a chemotherapeutic agent to the cell culture or sample, or to the individual.

In yet another aspect, the invention is a method of delivering a therapeutic agent to a cancerous cell in an individual by administering to the individual an effective amount of at least one member of a family of antibodies, which bind specifically to EphA2. In other embodiments, an anti-EphA2 antibody is delivered to an individual in combination with (including linked to) another therapeutic agent.

In some embodiments, the anti-EphA2 antibody is a humanized antibody derived from a named antibody family member herein (generally, but not necessarily, comprising one or more partial or intact CDRs of the antibody). In some embodiments, the anti-EphA2 antibody is a human antibody with one or more properties of the named antibody family member. In some embodiments, the chemotherapeutic agent (such as a toxin or a radioactive molecule) is delivered into the cancer cells (is internalized). In some embodiments, the agent is saporin.

In another aspect, the invention is a method of treating cancer in an individual comprising administering an effective amount of a composition comprising an anti-EphA2 antibody associated with (including linked to) a chemotherapeutic agent to the individual.

The present invention further provides methods for modulating, either by enhancing or reducing, the association of EphA2 with a cytoplasmic signaling partner. The association of EphA2 with a cytoplasmic signaling partner can be impacted by contacting an EphA2 molecule presenting on a cell surface, with an agent that modulates the binding of the signaling partner to EphA2. Agents which block or reduce EphA2 association with its binding and/or signaling partners can be used to modulate biological and pathological processes which are involved in EphA2 -mediated inflammation or immune responses. Pathological processes involving this action include tumor-associated cell growth.

Agents can be tested for their ability to block, reduce, enhance or otherwise modulate the association of EphA2 with a binding partner, such as an anti-EphA2 antibody. Specifically, an agent can be tested for the ability to modulate such an interaction by incubating a peptide comprising the EphA2 interaction site (typically in its native conformation as it exists on intact living cells) with a binding partner and a test agent, and determining whether the test agent reduces or enhances the binding of the binding partner to the EphA2 peptide. Agonists, antagonists, and other modulators are expressly contemplated.

In certain aspects, the invention is a method for aiding in the diagnosis of disease in an individual comprising the steps of (i) assaying for the presence of EphA2 in a blood or tissue sample obtained from an individual; (ii) detecting whether said sample has an increased amount of a EphA2 marker relative to a normal (non-diseased) blood or tissue sample; and (iii) correlating an increased amount of said marker to a positive diagnosis or correlating the absence of an increased amount of said marker to a negative diagnosis for disease. In certain embodiments, the marker is detected using an anti-EphA2 antibody. In certain embodiments, the method is effected by a technique selected from the group consisting of radionuclide imaging, flow cytometry, and immunohistochemistry.

In another aspect, the invention is a method of diagnosing cancer or metastatic cancer in an individual by detecting EphA2 on cells from the individual using the anti-EphA2 antibody or any EphA2 binding moiety (polypeptides, including, but not limited to, various antibodies and antibody derivatives) described herein. In some embodiments, the cancer is melanomas, breast, colon, lung, and prostate. In some embodiments, the method is detecting the level of EphA2 from cells. The presence of EphA2 is detected by detecting a complex between EphA2 and an EphA2 binding moiety. The term "detection" as used herein includes qualitative and/or quantitative detection (measuring levels) with or without reference to a control.

In another aspect, the invention is a method of treating cancer by administering an effective amount of a composition comprising the anti-EphA2 antibody, or any of the antibodies (including polypeptides) or polynucleotides embodiments described herein, including but not limited to the anti-EphA2 antibody associated with a therapeutic agent, an antibody comprising a fragment or a region of the anti-EphA2 antibody, a humanized antibody (generally, but not necessarily, comprising one or more CDRs of the anti-EphA2 antibody), a chimeric antibody comprising variable regions derived from variable regions of the anti-EphA2 antibody and constant regions derived from constant regions of a human antibody, or a human antibody with one or more properties of the anti-EphA2 antibody, sufficient to reduce growth of cancerous cells. In some embodiments, the cancer is melanomas, breast, colon, lung, or prostate.

In certain embodiments, the invention is a method of treating cancer in a patient, said method comprising administering to said patient a therapeutically effective amount of an EphA2 antibody that specifically binds to EphA2, and has at least one, and preferably two or more, of the following characteristics of SPL1, LUCA19, SG5 or LUCA40:
  a. the ability to bind to EphA2 on a cancer cell;
  b. the ability to bind to a portion of EphA2 that is exposed on the surface of a living cancer cell in vitro or in vivo;
  c. the ability to impede proliferation of tumor cells without increasing the phosphotyrosine content of EphA2;
  d. the ability to deliver a therapeutic agent or detectable marker to a cancer cell expressing EphA2; and
  e. the ability to deliver a therapeutic agent or detectable marker into a cancer cell expressing EphA2.

In another aspect, the invention is a method of inhibiting growth and/or proliferation of cancerous cells in an individual by administering to the individual an effective amount of a composition comprising the anti-EphA2 antibody, or any of the antibodies (including polypeptides) or polynucleotides embodiments described herein, including but not limited to the anti-EphA2 antibody associated with a therapeutic agent, an antibody comprising a fragment or a region of the anti-EphA2 antibody, a humanized antibody (generally, but not necessarily, comprising one or more CDRs of the anti-EphA2 antibody), a chimeric antibody comprising variable regions derived from variable regions of the anti-EphA2 antibody and constant regions derived from constant regions of a human antibody, or a human antibody with one or more properties of the anti-EphA2 antibody, sufficient to reduce growth of cancerous cells. In some embodiments, the cancer is melanomas, breast, colon, lung, or prostate.

In another aspect, the invention is a method of preventing or delaying development of metastasis, treating metastatic cancer, or inhibiting proliferation of metastatic cancer cells in an individual with cancer by administering an effective amount of a composition comprising the anti-EphA2 antibody, or any of the antibodies (including polypeptides) or polynucleotides embodiments described herein, including but not limited to the anti-EphA2 antibody associated with a therapeutic agent, an antibody comprising a fragment or a region of the anti-EphA2 antibody, or a humanized antibody (generally, but not necessarily, comprising one or more CDRs of the anti-EphA2 antibody), a chimeric antibody comprising variable regions derived from variable regions of the anti-EphA2 antibody and constant regions derived from constant regions of a human antibody, or a human antibody with one or more properties of the anti-EphA2 antibody, sufficient to reduce growth of cancerous cells. In some embodiments, the cancer is melanomas, breast, colon, lung, or prostate.

In another aspect, the invention is a method of delivering a therapeutic agent (such as a toxin, or a radioactive molecule) to cancerous cells in an individual by administering to the individual an effective amount of an EphA2 binding antibody or any EphA2 binding moiety (polypeptides, including but not limited to antibodies or antibody derivatives) described herein that are linked to a therapeutic agent (such as a toxin or a radioactive molecule). The EphA2 binding moiety includes, but not limited to the anti-EphA2 antibody, an antibody comprising a fragment or a region of the anti-EphA2 antibody, or a humanized antibody (generally, but not necessarily, comprising one or more CDRs of the anti-EphA2 antibody), a chimeric antibody comprising variable regions derived from variable regions of the anti-EphA2 antibody and constant regions derived from constant regions of a human antibody, or a human antibody with one or more properties of the anti-EphA2 antibody. In some embodiments, the cancerous cells are from melanomas, breast, colon, lung, or prostate cancer. In another embodiment, the therapeutic agent (such as a toxin or a radioactive molecule) is delivered into the cancerous cells (is internalized). Accordingly, the invention provides methods of inhibiting growth and/or proliferation of cancer cells such that the therapeutic agent is delivered into those cancer cells.

BRIEF DESCRIPTION OF THE DRAWINGS

FIG. 1 shows results of A549 tumor xenografts subcutaneously treated with SPL1 and their slow re-growth after cessation of dosing.

DETAILED DESCRIPTION OF THE INVENTION

The invention disclosed herein provides antibodies and polypeptides which bind to an antigen, EphA2 and methods of making and using these antibodies and polypeptides to diagnose and treat various diseases human cancers associated with expression and/or overexpression of EphA2. EphA2 has been shown to be present and its expression is increased in a variety of human cancers. Anti-EphA2 antibodies such as those produced by any one of the host cells identified in the following paragraph have been generated and have been shown to specifically bind to EphA2.

In accordance with the Budapest Treaty, the hybridoma which produces mLUCA19 has been deposited in the American Type Culture Collection (ATCC) 10801 University Blvd., Manassas Va. 20110-2209 on Mar. 20, 2003 with a Patent Deposit Designation of PTA-5070, the hybridoma which produces SPL1 has been deposited in the American Type Culture Collection (ATCC) on Jun. 8, 2004 with a Patent Deposit Designation of PTA-6059, the hybridoma which produces LUCA40 has been deposited in the American Type Culture Collection (ATCC) on Jun. 8, 2004 with a Patent Deposit Designation of PTA-6056, and the hybridoma which produces SG5 has been deposited in the American Type Culture Collection (ATCC) on Feb. 2, 2006 with a Patent Deposit Designation of PTA-7356.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

II. Definitions

EphA2 refers to that polypeptide antigen with a molecular weight of approximately 130 kD, against which the antibodies of the present invention are directed. As described in more detail herein, this antigen has more than one different epitope. Some of the preferred antibody embodiments of this invention are directed against one of two or more specific epitopes of the EphA2 antigen. It is currently believed that EphA2 is over-expressed in certain cancer cells in comparison to their normal tissue counterparts An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, naturally occurring variants, fusion proteins comprising an antibody portion with an antigen recognition site of the required specificity, humanized antibodies, chimeric antibodies, and any other modified configuration of the immunoglobulin molecule that comprises an antigen recognition site of the required specificity.

The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

"Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, six) which are altered with respect to the original antibody, which are also termed one or more CDRs "derived from" one or more CDRs from LUCA19, SPL1, SG5 or LUCA40.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an EphA2 epitope is an antibody that binds this EphA2 epitope with greater affinity, avidity, more readily, and/or with greater duration than it binds to other EphA2 epitopes or non-EphA2 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The term "immunologically active" in reference to an epitope being or "remaining immunologically active" refers to the ability of an antibody (e.g., anti-EphA2 antibody) to bind to the epitope under different conditions, for example, after the epitope has been subjected to reducing and denaturing conditions.

As used herein, the terms "LUCA19, SPL1, LUCA40, or SG5", "anti-EphA2 antibody" and "monoclonal anti-EphA2 antibody" are used interchangeably to refer to immunoglobulin produced by any of the host cells with a deposit number of ATCC No. PTA-5070, PTA-6056, or PTA-6059, or host cell SG.3.15B4.1F9 (ATCC No. PTA-7356) or progeny thereof. Different biological functions are associated with LUCA19, SPL1, SG5 or LUCA40, including, but not limited to, ability to bind to EphA2; ability to bind to EphA2 extracellular domain; ability to bind to EphA2 on cancer cells exposed on the surface of a living cell in vitro or in vivo; ability to deliver a chemotherapeutic agent to cancerous cells (such as ovarian, prostate, pancreatic, lung, colon, or breast cancer cells) expressing EphA2; ability to deliver a therapeutic agent or detectable marker into cancer cells expressing EphA2. As discussed herein, polypeptides (including antibodies) of the invention may have any one or more of these characteristics.

An "anti-EphA2 equivalent antibody" or "anti-EphA2 equivalent polypeptide" refers to an antibody or a polypeptide having one or more biological functions associated with an anti-EphA2 antibody, such as, for example binding specificity.

As used herein, "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

Agents that are employed in the methods of this invention can be randomly selected or rationally selected or designed. As used herein, an agent is said to be randomly selected when the agent is chosen randomly without considering the specific sequences involved in the association of EphA2 with its native binding partners or known antibodies. An example of randomly selected agents is the use of a chemical library or a peptide combinatorial library.

As used herein, an agent is said to be rationally selected or designed when the agent is chosen on a nonrandom basis that takes into account the sequence of the target site and/or its conformation in connection with the agent's action. With respect to anti-EphA2 agents, it is currently believed that there are at least three epitopes on EphA2 against which antibodies can be raised and therefore at least three sites of action for agents that block EphA2/anti-EphA2 interaction. This invention also encompasses agents that act at the sites of interaction between EphA2 and its native binding partner, although other ligands and their active EphA2-interactive sites are also encompassed within the scope of this invention, whether currently known or later identified. Agents can be rationally selected or rationally designed by utilizing the peptide sequences that make up the contact sites of the receptor/ligand and/or EphA2/anti-EphA2 antibody complex. For example, a rationally selected peptide agent can be a peptide whose amino acid sequence is identical to an epitope appearing on EphA2 as it is exposed on the surface of a living cell in its native environment. Such an agent will reduce or block the association of the anti-EphA2 antibody with EphA2, or the association of EphA2 with its native ligand, as desired, by binding to the anti-EphA2 antibody or to the native ligand.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE)) to the antibody, as well as indirect labeling of the probe or antibody by reactivity with a detectable substance.

As used herein, the term "association", with regard to the antibody, includes covalent and non-covalent attachment or binding to an agent (e.g., chemotherapeutic agent). The antibody can be associated with an agent (e.g., chemotherapeutic agent) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such that the agent's potency is not decreased.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof, for example, cells obtained from a tissue sample collected from an individual suspected of having cancer, in preferred embodiments from ovary, lung, prostate, pancreas, colon, and breast tissue. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

A "variable region" of an antibody refers to the variable region of the antibody light chain or the variable region of the antibody heavy chain, either alone or in combination.

A "constant region" of an antibody refers to the constant region of the antibody light chain or the constant region of the antibody heavy chain, either alone or in combination.

As used herein, "substantially pure" refers to material that is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "delaying development of metastasis" means to defer, hinder, slow, retard, stabilize, and/or postpone development of metastasis. This delay can be of varying lengths of time, depending on the history of the cancer and individual being treated. As is evident to one skilled in the art, a sufficient or significant delay can, in effect, encompass prevention, in that the individual does not develop the metastasis.

An "effective amount" of a drug, compound, or pharmaceutical composition is an amount sufficient to effect beneficial or desired results including, without limitation, clinical results such as shrinking the size of the tumor (in the cancer context, for example, breast or prostate cancer), retardation of cancerous cell growth, delaying the development of metastasis, decreasing one or more symptoms resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or destroy) neoplastic cells and/or to reduce and/or delay the development, or growth, of metastases of neoplastic cells, either directly or indirectly.

As is understood in the cancer clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including preferably clinical results. For purposes of this invention, beneficial or desired clinical results include, but are not limited to, one or more of the following: reducing the proliferation of (or destroying) neoplastic cells, reducing metastasis of neoplastic cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of patients.

As used herein, "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention, in that the individual does not develop the metastasis.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, pets (such as cats, dogs, horses), primates, mice and rats.

"Toxin" or "cytotoxin" refers to any substance, which effects an adverse response within a cell. For example, a toxin directed to a cancerous cell would have an adverse, sometimes deleterious effect, on the cancerous cell.

As used herein, "agent" refers to a biological, pharmaceutical, or chemical compound. Non-limiting examples include simple or complex organic or inorganic molecule, a peptide, a protein, an oligonucleotide, an antibody, an antibody derivative, or antibody fragment. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

As used herein, a "therapeutic agent" means any agent useful for therapy (here, generally in the cancer context) including anti-tumor drugs, toxins or cytotoxins, cytotoxin agents, and radioactive agents.

"Active immune response" refers to the development of, and on-going production of, antibodies in vivo directed against an antigen, in response to the administration of the antigen, or DNA vectors coding for that antigen, to the host mammal by intravenous, intramuscular, subcutaneous, or other mode of administration with or without an adjuvant. Active immune response can also include other aspects of the immune response, such as a cellular immune response.

Compositions and Methods of Making the Compositions

This invention encompasses compositions, including pharmaceutical compositions, comprising antibodies, polypeptides and proteins that bind to EphA2, and polynucleotides comprising sequences encoding antibodies, polypeptides and proteins that bind to EphA2. As used herein, compositions comprise one or more antibodies, polypeptides and/or proteins that bind to EphA2, and/or one or more polynucleotides comprising sequences encoding one or more antibodies, polypeptides and proteins that bind to EphA2. These compositions may further comprise suitable excipients, such as pharmaceutically acceptable excipients including buffers, which are well known in the art.

The present invention also encompasses various formulations of LUCA19, SPL1, SG5 or LUCA40 and equivalent antibodies or polypeptide fragments (e.g., Fab, Fab', F(ab')$_2$, Fv, Fc, etc.), chimeric antibodies, single chain (ScFv), mutants thereof, fusion proteins comprising an antibody portion, humanized antibodies, and any other modified configuration of LUCA19, SPL1, SG5 or LUCA40 that comprises an antigen (EphA2), recognition site of the required specificity. The invention also provides human antibodies displaying one or more of the biological characteristics of LUCA19, SPL1, SG5 or LUCA40. The equivalent antibodies of LUCA19, SPL1, SG5 or LUCA40 (including humanized antibodies and human antibodies), polypeptide fragments of LUCA19, SPL1, SG5 or LUCA40, and polypeptides comprising any of these fragments are identified and characterized by one or more characteristics of LUCA19, SPL1, SG5 or LUCA40.

In some embodiments, the antibodies, polypeptides and proteins of the invention that bind to EphA2 are antibodies, polypeptides and proteins that competitively inhibit preferential binding of LUCA19, SPL1, SG5 or LUCA40 to EphA2 or that preferentially bind to the same epitope on EphA2 as the anti-EphA2 antibody preferentially binds.

Accordingly, the invention provides any of the following (or compositions, including pharmaceutical compositions), comprising any of the following: (a) anti-EphA2 antibody produced by the host cell with a deposit number of ATCC No. PTA-5070, PTA-6056, or PTA-6059, or host cell SG3.15B4.1F9 (PTA-7356) or its progeny; (b) a humanized form of anti-EphA2 antibody; (c) an antibody comprising one or more of the light chain and/or heavy chain variable regions of anti-EphA2 antibody; (d) a chimeric antibody comprising variable regions homologous or derived from variable regions of a heavy chain and a light chain of anti-EphA2 antibody, and constant regions homologous or derived from constant regions of a heavy chain and a light chain of a human antibody; (e) an antibody comprising one or more of the light chain and/or heavy chain CDRs (at least one, two, three, four, five, or six) of LUCA19, SPL1, SG5 or LUCA40; (f) an antibody comprising a heavy and/or a light chain of LUCA19, SPL1, SG5 or LUCA40; (g) a human antibody that is equivalent to LUCA19, SPL1, SG5 or LUCA40. A humanized form of the antibody may or may not have CDRs identical to LUCA19, SPL1, LUCA40, or SG5 or antibody produced by the host cell with a deposit number of ATCC No. PTA-5070, PTA-6056, or PTA-6059 or host cell SG3.15B4.1F9 (ATCC No. PTA-7356). Determination of CDR regions is well within the skill of the art. In some embodiments, the invention provides an antibody which comprises at least one CDR that is substantially homologous to at least one CDR, at least two, at least three, at least four, at least 5 CDRs of LUCA19, SPL1, SG5 or LUCA40 (or, in some embodiments substantially homologous to all 6 CDRs of LUCA19, SPL1, SG5 or LUCA40, or derived from LUCA19, SPL1, LUCA40, or SG5), or antibody produced by the host cell with a deposit number of ATCC No. PTA-5070, PTA-6056, PTA-6059, or host cell SG3.15B4.1F9 (ATCC No. PTA-XXXX). Other embodiments include antibodies that have at least two, three, four, five, or six CDR(s) that are substantially homologous to at least two, three, four, five or six CDRs of LUCA19, SPL1 LUCA40, or SG5 or derived from LUCA19, SPL1, LUCA40, or SG5, or antibody produced by the host cell with a deposit number of ATCC No. PTA-5070, PTA-6056, PTA-6059 or host cell SG3.15B.1F9. It is understood that, for purposes of this invention, binding specificity and overall activity (which may be in terms of reducing the growth and/or proliferation of cancerous cells, inducing apoptotic cell death in the cancer cell, delaying the development of metastasis, and treating palliatively) is generally retained, although the extent of activity may vary compared to LUCA19, SPL1, SG5 or LUCA40 (may be greater or lesser). The invention also provides methods of making any of these antibodies. Methods of making antibodies are known in the art and are described herein.

The invention also provides polypeptides comprising an amino acid sequence of the antibodies of the invention, such as LUCA19, SPL1, SG5 or LUCA40. In some embodiments, the polypeptide comprises one or more of the light chain and heavy chain variable regions of the anti-EphA2 antibody. In some embodiments, the polypeptide comprises one or more of the light chain and heavy chain CDRs of LUCA19, SPL1, SG5 or LUCA40. In some embodiments, the polypeptide comprises three CDRs of the light chain and heavy chain of LUCA19, SPL1, SG5 or LUCA40. In some embodiments, the polypeptide comprises an amino acid sequence of LUCA19, SPL1, SG5 or LUCA40 that has any of the following: at least 5 contiguous amino acids of a sequence of LUCA19, SPL1, SG5 or LUCA40, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of LUCA19, SPL1, SG5 or LUCA40. In one embodiment, the variable region is from a light chain of LUCA19, SPL1, SG5 or LUCA40. In another embodiment, the variable region is from a heavy chain of LUCA19, SPL1, SG5 or LUCA40. In another embodiment, the 5 (or more) contiguous amino acids are from a complementarity-determining region (CDR) of LUCA19, SPL1, SG5 or LUCA40.

Antibodies may be polyclonal (e.g., not homogeneous) or monoclonal. Methods of making monoclonal antibodies are known in the art. One method which may be employed is the method of Kohler and Milstein, Nature 256:495-497 (1975) or a modification thereof. In general, a mouse or rat is used for immunization but other animals may also be used. The immunogen can be, but is not limited to, primary cells, cultured cell lines, cancerous cells, nucleic acids, tissue, or peptides. Full length EphA2 or any fragments of EphA2 (e.g., extracellular domain), or EphA2 expressing cancer cells are used as immunogen. Cells used for immunogen, for example, EphA2 expressing cancer cells may be cultured for a period of time (at least 24 hours) prior to their use as an immunogen. Cells may be used as immunogens by themselves or in combination with a non-denaturing adjuvant, such as Ribi. In general, cells should be kept intact and preferably viable when used as immunogen. Methods of generating antibodies using intact cells as immunogen are described in WO 00/37503. Intact cells may allow antigens to be better detected than ruptured cells. In addition, monoclonal antibodies generated using intact cells as immunogen are most likely against an antigenic determinant on the cell surface or against extracellular domain of a transmembrane receptor. Use of denaturing or harsh adjuvants, e.g., Freud's adjuvant, may rupture the cells and therefore is discouraged. The immunogen may be administered multiple times at periodic intervals such as, bi-weekly, or weekly, or may be administered in such a way as to maintain viability in the animal (e.g., in a tissue recombinant).

To monitor the antibody response, a small biological sample (e.g., blood) may be obtained from the animal and tested for antibody titer against the immunogen. The spleen and/or several large lymph nodes can be removed and dissociated into single cells. If desired, the spleen cells may be screened (after removal of non-specifically adherent cells) by applying a cell suspension to a plate or to a well coated with the antigen. B-cells, expressing membrane-bound immunoglobulin specific for the antigen, will bind to the plate, and are not rinsed away with the rest of the suspension. Resulting B-cells, or all dissociated spleen cells, can then be fused with myeloma cells (e.g., X63-Ag8.653 and those from the Salk Institute, Cell Distribution Center, San Diego, Calif.). Polyethylene glycol (PEG) may be used to fuse spleen or lymphocytes with myeloma cells to form a hybridoma. The hybridoma is then cultured in a selective medium (e.g., hypoxanthine, aminopterin, thymidine medium, otherwise known as "HAT medium"). The resulting hybridomas are then plated by limiting dilution, and are assayed for the production of antibodies that bind specifically to the immunogen (e.g., surface of cancer cell lines, EphA2, etc.) using FACS, immunohistochemistry (IHC screening), and Western blot. The selected monoclonal antibody-secreting hybridomas are then cultured either in vitro (e.g., in tissue culture bottles or hollow fiber reactors), or in vivo (e.g., as ascites in mice). Methods of culturing hybridoma under conditions to generate the anti-EphA2 antibody, and purifying the antibody are known in the art.

Monoclonal antibody-secreting hybridomas described above can be selected for producing antibodies that bind preferentially to the epitope on EphA2 that the anti-EphA2 antibody preferentially binds. Methods of selecting such antibody are known in the art. For example, binding competition assays can be used to determine whether an antibody binds to the same epitope as does LUCA19, SPL1, SG5 or LUCA40. An antibody's competition with LUCA19, SPL1, SG5 or LUCA40 for binding to EphA2 indicates that the antibody binds preferentially to the epitope that LUCA19, SPL1, SG5 or LUCA40 binds. Binding competition assays are well known in the art. Binding competition assays, which can be configured in a number of different formats, using either labeled antigen or labeled antibody. Usually, the antigen is immobilized on a 96-well plate, and the ability of unlabeled antibodies to block the binding of labeled antibodies is measured using radioactive or enzyme labels. Polypeptides that bind preferentially to the epitope on EphA2 that the anti-EphA2 antibody binds preferentially can also be tested and identified using similar methods.

As another alternative to the cell fusion technique, EBV immortalized B cells may be used to produce monoclonal antibodies of the subject invention. The hybridomas are expanded and subcloned, if desired, and supernatants are assayed for anti-immunogen activity by conventional assay procedures (e.g., FACS, IHC, radioimmunoassay, enzyme immunoassay, fluorescence immunoassay, etc.).

In another alternative, the antibodies can be made recombinantly. Methods for making recombinant antibodies are well known in the art. Monoclonal antibody LUCA19, SPL1, SG5 or LUCA40 and any other equivalent antibodies can be sequenced and produced recombinantly in vitro. In one embodiment, LUCA19, SPL1, SG5 or LUCA40 is sequenced and the polynucleotide sequence is then cloned into a vector for expression or propagation. The sequence encoding the antibody of interest may be maintained in a vector in a host cell and the host cell can then be expanded and frozen for future use. In another alternative, antibodies may be made recombinantly by phage display technology. See, for example, U.S. Pat. Nos. 5,565,332; 5,580,717; 5,733,743; 6,265,150; and Winter et al., Annu. Rev. Immunol. (1994) 12:433-455.

In another alternative, the anti-EphA2 antibody or any other antibodies or protein of interest may be subjected to sequencing by Edman degradation, which is well known to those of skill in the art. The peptide information generated from mass spectrometry or Edman degradation can be used to design probes or primers that are used to clone the protein of interest.

An alternative method of cloning the protein of interest is by "panning" using EphA2 for cells expressing the antibody or protein of interest. The "panning" procedure is conducted by obtaining a cDNA library from tissues or cells that express the antibody or protein of interest, over-expressing the cDNAs in a second cell type, and screening the transfected cells of the second cell type for a specific binding to EphA2. Detailed descriptions of the methods used in cloning mammalian genes coding for cell surface proteins by "panning" can be found in the art. See, for example, Aruffo, A. and Seed, B. *Proc. Natl. Acad. Sci. USA,* 84, 8573-8577 (1987) and Stephan, J. et al., *Endocrinology* 140: 5841-5854 (1999).

cDNAs can be obtained by reverse transcribing the mRNAs from a particular cell type according to standard methods in the art. Specifically, mRNA can be isolated using various lytic enzymes or chemical solutions according to the procedures set forth in Sambrook, et al. supra or extracted by commercially available nucleic-acid-binding resins following the accompanying instructions provided by manufacturers (e.g., Qiagen, Invitrogen, Promega). The synthesized cDNAs are then introduced into an expression vector to produce the antibody or protein of interest in cells of a second type. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, and cosmids.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to EphA2 is effected by an immunoassay or FACS. A cell over-expressing the antibody or protein of interest can be identified.

The invention includes polypeptides comprising an amino acid sequence of the antibodies of this invention, such as LUCA19, SPL1, SG5 or LUCA40. The polypeptides of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, a LUCA19, SPL1, SG5 or LUCA40 polypeptide could be produced by an automated polypeptide synthesizer employing the solid phase method.

The invention also encompasses single chain variable region fragments ("scFv") of antibodies of this invention, such as LUCA19, SPL1, SG5 or LUCA40. Single chain variable region fragments are made by linking light and/or heavy chain variable regions by using a short linking peptide. Bird et al. (1988) *Science* 242: 423-426. For example a linking peptide can bridge approximately 3.5 nm between the carboxy terminus of one variable region and the amino terminus of the other variable region. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

The invention includes modifications to antibodies, such as anti-EphA2 antibody, including functionally equivalent antibodies and polypeptides of LUCA19, SPL1, SG5 or LUCA40 that do not significantly affect their properties and variants which have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tryosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified LUCA19, SPL1, SG5 or LUCA40 polypeptides are made using established procedures in the art and can be screened using standard assays known in the art, some of which are described below and in the Examples.

The invention also encompasses fusion proteins comprising one or more fragments or regions from the antibodies of this invention, such as LUCA19, SPL1, SG5 or LUCA40. In one embodiment, a fusion polypeptide is provided that comprises at least 10 contiguous amino acids of variable light chain region and at least 10 amino acids of variable heavy chain region. In another embodiment, the fusion polypeptide contains a heterologous immunoglobulin constant region. In another embodiment, the fusion polypeptide contains a light chain variable region and a heavy chain variable region of LUCA19, SPL1, SG5 or LUCA40. For purposes of this invention, a LUCA19, SPL1, SG5 or LUCA40 fusion protein contains one or more LUCA19, SPL1, SG5 or LUCA40 polypeptides and another amino acid sequence to which it is not attached in the native molecule, for example, a heterologous sequence or a homologous sequence from another region. A LUCA19, SPL1, SG5 or LUCA40 polypeptide can be created by methods known in the art, for example, synthetically or recombinantly.

In another embodiment, LUCA19, SPL1, SG5 or LUCA40 chimeras are provided in which the heavy and/or light chains are fusion proteins. In some embodiments, the constant domain of the chains is from one particular species and/or class, and the variable domains are from a different species and/or class. For instance, a chimeric antibody (in some embodiments) is one in which the constant regions are derived from human origin, and the variable regions are homologous or derived from LUCA19, SPL1, SG5 or LUCA40 (i.e., murine). Also embodied within the invention is an antibody with a humanized variable region, in which (in some embodiments) the CDR regions comprise LUCA19, SPL1, SG5 or LUCA40 amino acid sequences, while the framework regions are derived from human sequences. Other forms of humanized antibodies are known in the art and described herein. Also embodied are functional fragments of chimeras. An example is a humanized Fab fragment, which contains a human hinge region, a human first constant region, a human kappa light or heavy chain constant region, and the variable region of light and/or heavy chain from LUCA19, SPL1, SG5 or LUCA40. The humanized LUCA19, SPL1, SG5 or LUCA40 Fab fragments can in turn be made to form Fab dimers. Typically, the LUCA19, SPL1, SG5 or LUCA40 fusion proteins and LUCA19, SPL1, SG5 or LUCA40 chimeras of this invention are made by preparing an expressing a polynucleotide encoding them using recombinant methods described herein, although they may also be prepared by other means known in the art, including, for example, chemical synthesis. See, for example, U.S. Pat. Nos. 5,807,715; 4,816,567; and 6,331,415.

The invention also encompasses humanized antibodies. The polynucleotide sequence of an antibody, such as LUCA19, SPL1, SG5 or LUCA40 or other equivalent antibodies may be used for genetic manipulation to generate a "humanized" antibody, or to improve the affinity, or other characteristics of the antibody. The general principle in humanizing an antibody involves retaining the basic sequence of the antigen-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. For example, the constant region may be engineered to more resemble human constant regions to avoid immune response if the antibody is used in clinical trials and treatments in humans. See, for example, U.S. Pat. Nos. 5,997,867 and 5,866,692.

A number of "humanized" antibody molecules comprising an antigen-binding site derived from a non-human immunoglobulin have been described, including chimeric antibodies having rodent V regions and their associated complementarity determining regions (CDRs) fused to human constant domains. See, for example, Winter et al. *Nature* 349:293-299 (1991); Lobuglio et al. *Proc. Nat. Acad. Sci. USA* 86:4220-4224 (1989); Shaw et al. *J Immunol.* 138:4534-4538 (1987); and Brown et al. Cancer Res. 47:3577-3583 (1987). Other references describe rodent CDRs grafted into a human supporting framework region (FR) prior to fusion with an appropriate human antibody constant domain. See, for example, Riechmann et al. *Nature* 332:323-327 (1988); Verhoeyen et al. Science 239:1534-1536 (1988); and Jones et al. *Nature* 321:522-525 (1986). Another reference describes rodent CDRs supported by recombinantly veneered rodent framework regions. See, for example, European Patent Publication No. 519,596. These "humanized" molecules are designed to minimize unwanted immunological response toward rodent antihuman antibody molecules that limits the duration and effectiveness of therapeutic applications of those moieties in human recipients. Other methods of humanizing antibodies that may also be utilized are disclosed by Daugherty et al., *Nucl. Acids Res.,* 19:2471-2476 (1991) and in U.S. Pat. Nos. 6,180,377; 6,054,297; 5,997,867; 5,866,692; 6,210,671; 6,350,861; and PCT WO 01/27160.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

This invention also provides compositions comprising LUCA19, SPL1, SG5 or LUCA40 or LUCA19, SPL1, SG5 or LUCA40 equivalent antibodies or polypeptides conjugated (for example, linked) to a therapeutic agent, such as a radioactive molecule, a toxin (e.g., calicheamicin), or a chemotherapeutic molecule, or to liposomes or other vesicles containing chemotherapeutic compounds. The compositions, when administered to an individual, can target these agents to a cancer cell expressing EphA2 recognized by the antibody or polypeptide(s) and thus can, for example, eliminate cancerous cells and/or suppress proliferation and/or growth of cancerous cells. For simplicity, reference will be made generally to LUCA19, SPL1, SG5 or LUCA40 or antibodies with the understanding that these methods apply to any of the EphA2 binding embodiments described herein. With these methods, conjugation generally refers to linking these components as described herein. The linking (which is generally fixing these components in proximate association at least for administration) can be achieved in any number of ways, as described below.

A radioactive molecule of this invention includes any radioisotope that is effective in destroying a cancerous cell. Examples include, but not limited to, cobalt-60 and X-rays. Additionally, naturally occurring radioactive elements such as uranium, radium, and thorium that typically represent mixtures of radioisotopes, are suitable examples of a radioactive molecule.

A toxin of the invention include, but not limited to, taxol, cytochalasin B, gramicidin D, ethidium bromide, emetine, mitomycin, etoposide, tenoposide, vincristine, vinblastine, Colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. The antibodies of the invention can be internalized within the carcinoma cells to which they bind and are therefore particularly useful for therapeutic applications, for example, delivering into the cells toxins that need to be internalized for their adverse activity. Examples of such toxins include, but not limited to, saporin, calicheamicin, auristatin, and maytansinoid.

The antibodies or polypeptides of the invention can be conjugated (linked) to a radioactive molecule, a toxin, or other therapeutic agents, or to liposomes or other vesicles containing therapeutic agents covalently or non-covalently, directly or indirectly. The antibody may be linked to the radioactive molecule, the toxin, or the therapeutic molecule at any location along the antibody so long as the antibody is able to bind its target EphA2.

A toxin or a therapeutic agent may be coupled (e.g., covalently bonded) to a suitable monoclonal antibody either directly or indirectly (e.g., via a linker group, or, alternatively, via a linking molecule with appropriate attachment sites, such as a platform molecule as described in U.S. Pat. No. 5,552,391). The toxin and therapeutic agent of the present invention can be coupled directly to the particular targeting proteins using methods known in the art. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies or polypeptides can also be linked to a therapeutic agent via a microcarrier. Microcarrier refers to a biodegradable or a non-biodegradable particle which is insoluble in water and which has a size of less than about 150, 120 or 100 mm in size, more commonly less than about 50-60 μm, preferably less than about 10, 5, 2.5, 2 or 1.5 μm. Microcarriers include "nanocarriers", which are microcarriers have a size of less than about 1 μm, preferably less than about 500 nm. Such particles are known in the art. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5]undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, and phospholipid, adjuvant-active saponin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers that deviate from spherical shape are also acceptable (e.g., ellipsoid, rod-shaped, etc.). Due to their insoluble nature (with respect to water), microcarriers are filterable from water and water-based (aqueous) solutions.

The antibody or polypeptide conjugates of the present invention may include a bifunctional linker that contains both a group capable of coupling to a toxic agent or therapeutic agent and a group capable of coupling to the antibody. A linker can function as a spacer to distance an antibody from an agent in order to avoid interference with binding capabilities. A linker can be cleavable or non-cleavable. A linker can also serve to increase the chemical reactivity of a substituent on an agent or an antibody, and thus increase the coupling efficiency. An increase in chemical reactivity may also facilitate the use of agents, or functional groups on agents, which otherwise would not be possible. The bifunctional linker can be coupled to the antibody by means that are known in the art. For example, a linker containing an active ester moiety, such as an N-hydroxysuccinimide ester, can be used for coupling to lysine residues in the antibody via an amide linkage. In another example, a linker containing a nucleophilic amine or hydrazine residue can be coupled to aldehyde groups produced by glycolytic oxidation of antibody carbohydrate residues. In addition to these direct methods of coupling, the linker can be indirectly coupled to the antibody by means of an intermediate carrier such as an aminodextran. In these embodiments the modified linkage is via either lysine, carbohydrate, or an intermediate carrier. In one embodiment, the linker is coupled site-selectively to free thiol residues in the protein. Moieties that are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine. Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavored. See, for example, U.S. Pat. No. 6,441,163 for preparation of conjugates of maytansinoids and antibody via a disulfide moiety.

One of the cleavable linkers that can be used for the preparation of antibody-drug conjugates is an acid-labile linker based on cis-aconitic acid that takes advantage of the acidic environment of different intracellular compartments such as the endosomes encountered during receptor mediated endocytosis and the lysosomes. See, for example, Shen et al., *Biochem. Biophys. Res. Commun.* 102:1048-1054 (1981) for the preparation of conjugates of daunorubicin with macromolecular carriers; Yang et al., *J. Natl. Canc. Inst.* 80:1154-1159 (1988) for the preparation of conjugates of daunorubicin to an anti-melanoma antibody; Dillman et al., *Cancer Res.* 48:6097-6102 (1988) for using an acid-labile linker in a similar fashion to prepare conjugates of daunorubicin with an anti-T cell antibody; Trouet et al., *Proc. Natl. Acad. Sci.* 79:626-629 (1982) for linking daunorubicin to an antibody via a peptide spacer arm.

An antibody (or polypeptide) of this invention may be conjugated (linked) to a radioactive molecule by any method known to the art. For a discussion of methods for radiolabeling antibody see "Cancer Therapy with Monoclonal AntibodiesT", D. M. Goldenberg ed. (CRC Press, Boca Raton, 1995).

An antibody (or polypeptide) of this invention may be linked to a labeling agent (alternatively termed "label") such as a fluorescent molecule, a radioactive molecule or any others labels known in the art. Labels are known in the art that generally provide (either directly or indirectly) a signal.

The ability of the antibodies, polypeptides and proteins of this invention, such as ability to inhibit growth of cancerous cells expressing EphA2, ability to delay development of metastasis in an individual with cancer expressing EphA2, ability to deliver a therapeutic agent, such as a toxin, or a radioactive compound, to cancerous cells expressing EphA2, including ability to deliver a therapeutic agent into cancerous cells expressing EphA2, may be tested using methods known in the art, some of which are described in the Examples.

The invention also provides compositions (including pharmaceutical compositions) comprising anti-EphA2 antibody or LUCA19, SPL1, SG5 or LUCA40 equivalent antibodies (which, as this disclosure makes clear, include all of the antibodies described herein) or polypeptides and a therapeutic agent.

Methods for Screening Monoclonal Antibodies

Several methods may be used to further screen monoclonal antibodies that bind to EphA2 on cancerous cells. One method that may be employed is immunohistochemistry (IHC). Standard immunohistochemical techniques are known to those of average skill in the art. See, for example, *Animal Cell Culture Methods* (J. P. Mather and D. Barnes, eds., Academic Press, Vol. 57, Ch. 18 and 19, pp. 314-350, 1998). Biological samples (e.g., tissues) may be obtained from biopsies, autopsies, or necropsies. To ascertain if EphA2 is present only on cancerous cells, LUCA19, SPL1, SG5 or LUCA40 may be used to detect the presence of EphA2 on tissues from individuals with cancer while other non-cancerous tissues from the individual suffering from cancer or tissues from individuals without cancer are used as a control. The tissue can be embedded in a solid or semi-solid substance that prevents damage during freezing (e.g., agarose gel or OCT) and then sectioned for staining. Cancers from different organs and at different grades can be used to screen monoclonal antibodies. Examples of tissues that may be used for screening purposes include but are not limited to ovary, breast, lung, prostate, colon, kidney, skin, thyroid, brain, heart, liver, stomach, nerve, blood vessels, bone, upper digestive tract, and pancreas. Examples of different cancer types that may be used for screening purposes include but are not limited to carcinomas, adenocarcinomas, sarcomas, adenosarcomas, lymphomas, and leukemias.

In yet another alternative, cancerous cells lines such as SK-Ov-3 (ATCC #HTB 77), LnCap (ATCC #CRL-1740), COLO 205 (ATCC #CCL 222), A549 (ATCC #CCL 185), PANC-1 (ATCC #CRL 1469), SK-BR-3 (ATCC #HTB 30), SK-MES-1 (ATCC #HTB 58), HT-29 (HTB-38), SW 480 (ATCC #CCL 228), AsPC-1 (ATCC #CRL 1682), Capan-1 (ATCC #HTB 79), CFPAC-1 (ATCC #CRL 1918), HPAF-II (ATCC #CRL-1997), HS-700T (ATCC #HTB 147), Du-145 (ATCC #HTB-81), CaLu-1 (ATCC #HTB-54), 786-0 (ATCC #CRL-1932). CaKi-2 (ATCC #HTB-47), A498 (ATCC #HTB-44), BT474 (ATCC #HTB-20), and PC-3 (ATCC #CRL 1435) and normal cells from their respective tissues may be used to screen for monoclonal antibodies which are specific for cancerous tissue. Primary, or low passage, cell cultures derived from normal tissues from different organs, including but not limited to, ovary, breast, lung, prostate, colon, kidney, skin, thyroid, aortic smooth muscle, and endothelial cells can be used as negative controls. The cancerous or non-cancerous cells can be grown on glass slides or coverslips, or on plastic surfaces, or prepared in a CellArray™, as described in WO 01/43869, and screened for the binding of antibody using IHC as described above for tissues. Alternatively, cells may be removed from the growth surface using non-proteolytic means and spun into a pellet which is then embedded and treated as tissues for IHC analysis as described above. In another alternative, single cells may be screened by incubating with the primary antibody, a secondary "reporter" antibody linked to a fluorescent molecule and then analyzed using a fluorescent activated cell-sorting (FACS) machine.

Several different detection systems may be utilized to detect binding of antibodies to tissue section. Typically, immunohistochemistry involves the binding of a primary antibody to the tissue and then a secondary antibody reactive against the species from the primary antibody was generated and conjugated to a detectable marker (e.g., horseradish peroxidase, HRP, or diaminobenzedine, DAB). One alternative method that may be used is polyclonal mirror image complementary antibodies or polyMICA. PolyMICA (polyclonal Mirror Image Complementary Antibodies) technique, described by D. C. Mangham and P. G. Isaacson (*Histopathology* (1999) 35(2):129-33), can be used to test binding of primary antibodies (e.g., LUCA19, SPL1, SG5 or LUCA40) to normal and cancerous tissue. Several kinds of polyMICA™ Detection kits are commercially available from The Binding Site Limited (P.O. Box 4073 Birmingham B29 6AT England). Product No. HK004.D is a polyMICA™ Detection kit which uses DAB chromagen. Product No. HK004.A is a polyMICA™ Detection kit which uses AEC chromagen. Alternatively, the primary antibody may be directly labeled with the detectable marker.

The first step in IHC screening to select for an appropriate antibody is the binding of primary antibodies raised in mice (e.g., LUCA19, SPL1, SG5 or LUCA40) to one or more immunogens (e.g., cells or tissue samples). In one embodiment, the tissue sample is sections of frozen tissue from different organs. The cells or tissue samples can be either cancerous or non-cancerous.

Frozen tissues can be prepared, sectioned, with or without fixation, and IHC performed by any of a number of methods known to one familiar with the art. See, for example, Stephan et al. *Dev. Biol.* 212: 264-277 (1999), and Stephan et al. *Endocrinology* 140: 5841-54 (1999).

Monoclonal antibodies that are cross-reactive with human cells and that bind to cancerous cells or tissues, but not to normal cells or tissues to the same degree, are selected. Monoclonal antibodies that bind to antigens expressed on one or more cancer types but not to normal cells are also selected. LUCA19, SPL1, SG5 or LUCA40 is an example of an antibody that binds to the antigen EphA2 present on a number of different cancers, but has limited binding to normal tissues. Epitope mapping may be used to further characterize the antibody. Commercially available services (e.g., Pepscan Systems, P.O. Box 2098, 8203 AB Lelystad, The Netherlands) may be used to determine the epitope(s) on the antigen EphA2 to which an antibody, such as LUCA19, SPL1, SG5 or LUCA40, binds.

Methods of Diagnosing Cancer Using LUCA19, SPL1, SG5 or LUCA40, Equivalent Antibodies or Polypeptides that Bind to EphA2

Monoclonal anti-EphA2 antibody and equivalent antibodies or polypeptides derivatives of LUCA19, SPL1, SG5 or LUCA40 which bind EphA2 made by the methods disclosed herein may be used to identify or detect the presence or absence of cancerous cells in a variety of tissues, including but not limited to, ovary, breast, lung, prostate, colon, kidney, skin, thyroid, brain, heart, liver, stomach, nerve, blood vessels, bone, upper digestive tract, and pancreas for purposes of diagnosis. For simplicity, reference will be made generally to LUCA19, SPL1, SG5 or LUCA40 or antibodies with the understanding that these methods apply to any of the EphA2 binding embodiments described herein. Detection generally involves contacting cells with an antibody or a polypeptide described herein that binds to EphA2 and the formation of a complex between EphA2 and an antibody (e.g., LUCA19, SPL1, SG5 or LUCA40, a humanized antibody of LUCA19, SPL1, SG5 or LUCA40, a human antibody or any other EphA2 binding moiety) that binds specifically to EphA2. The formation of such a complex can be in vitro or in vivo. Without being bound by theory, monoclonal anti-EphA2 antibody can bind to EphA2 through the extracellular domain of EphA2. As used herein, detection may include qualitative and/or quantitative detection and may include comparing the level measured to a normal cell for an increased level of expression of EphA2 in cancerous cells.

One method of using the antibodies for diagnosis is in vivo tumor imaging by linking the antibody to a labeling moiety (e.g., a fluorescent agent, a radioactive or radioopaque agent), administering the antibody to the patient and using an x-ray or other imaging machine to visualize the localization of the labeled antibody at the surface of cancer cells expressing the antigen. Labeling moieties are known in the art.

In other methods, the cancerous cells are removed and the tissue prepared for immunohistochemistry by methods well known in the art (e.g., embedding in a freezing compound, freezing and sectioning, with or without fixation; fixation and paraffin embedding with or without various methods of antigen retrieval and counterstaining). The monoclonal antibodies may also be used to identify neoplasms at different stages of development. The antibodies may also be used to determine which patients' tumors express the antigen on their surface at a pre-determined level and are thus candidates for immunotherapy using antibodies directed against said antigen.

Antibodies (or polypeptides) recognizing the antigen may also be used to create diagnostic immunoassays for detecting antigen released or secreted from living or dying cancer cells in bodily fluids, including but not limited to, blood, saliva, urine, pulmonary fluid, or ascites fluid. As discussed in further detail in the Examples, LUCA19, SPL1, SG5 or LUCA40 can bind to various forms cancer in different stages from tissues including but not limited to melanomas, breast, lung, prostate, and colon. Methods of using LUCA19, SPL1, SG5 or LUCA40 for diagnostic purposes is useful both before and after any form of anti-cancer treatment, e.g., chemotherapy or radiation therapy, to determine which tumors are most likely to respond to a given treatment, patient prognosis, tumor subtype or origin of metastatic disease, and progression of the disease or response to treatment.

Methods of Using LUCA19, SPL1, SG5 or LUCA40, or Equivalent Antibodies or Polypeptides for Therapeutic Purposes Monoclonal anti-EphA2 antibody and equivalent antibodies (as well as other polypeptides embodiments of the invention) made by the methods disclosed herein may be used for therapeutic purposes in individuals with cancer, including but not limited to melanomas, breast, lung, colon, or prostate cancer. These therapeutic methods also apply to the linked embodiments described above. For simplicity, reference will be made generally to LUCA19, SPL1, SG5 or LUCA40 or antibodies with the understanding that these methods apply to any of the EphA2 binding embodiments described herein, including but not limited to humanized antibodies and human antibodies described herein including linked embodiments. Therapy with LUCA19, SPL1, SG5 or LUCA40 can involve formation of complexes of such antibody and EphA2 both in vitro and/or in vivo as described above. In one embodiment, monoclonal anti-EphA2 antibody can bind to and reduce the growth and/or proliferation of cancerous cells. In another embodiment, monoclonal anti-EphA2 antibody can bind to and induce apoptotic cell death in the cancer cell. In another embodiment, monoclonal anti-EphA2 antibody can bind to cancerous cells and delay the development of metastasis. In another embodiment, monoclonal anti-EphA2 antibody can bind to cancerous cells and deliver a therapeutic agent (such as a toxin, or a radioactive compound) linked to LUCA19, SPL1, SG5 or LUCA40 to cancerous cells. For some embodiments, therapeutic agent (such as a toxin) is introduced into a cell (i.e., is internalized). Particularly suitable agents for these methods include agents that are active inside the cell. Examples of such agents include but not limited to saporin, calicheamicin, auristatin, and maytansinoid. Generally, in these embodiments an effective amount (an amount sufficient to deliver a therapeutic agent to and into target cancerous cells) is administered to an individual. In yet another embodiment, an individual with cancer is given palliative treatment with LUCA19, SPL1, SG5 or LUCA40. Palliative treatment of a cancer patient involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

This invention also provides methods of inhibiting growth and/or proliferation of cancer cells using LUCA19, SPL1, SG5 or LUCA40 antibody or an antibody which preferentially binds to the same epitope as the epitope to which any of LUCA19, SPL1, SG5 or LUCA40 preferentially binds.

In yet another embodiment, LUCA19, SPL1, SG5 or LUCA40 or any of the EphA2 embodiments described herein can bind to EphA2 expressing cancerous cells and induces an active immune response against the cancerous cells expressing EphA2. In some cases, the active immune response can cause the death of the cancerous cells (e.g., LUCA19, SPL1, SG5 or LUCA40 binding to cancer cells inducing apoptotic or oncotic cell death), or inhibit the growth (e.g., block cells cycle progression) of the cancerous cells. In other cases, LUCA19, SPL1, SG5 or LUCA40 or any of the EphA2 antibodies described herein can bind to cancerous cells and antibody-dependent cellular cytotoxicity (ADCC) can eliminate cancerous cells to which LUCA19, SPL1, SG5 or LUCA40 binds. Accordingly, the invention provides methods of stimulating an immune response comprising administering any of the compositions described herein.

The anti-EphA2 antibody may be administered with agents that enhance or direct an individual's own immune response, such as an agent that strengthens ADCC. In one embodiment, at least one fucose residue present in an anit-EphA2 antibody is removed from the oligosaccharides of that antibody, a modification to enhance ADCC. In similar embodiments, fucose residues present in an anti-EphA2 antibody are modified to alter their composition to the extent required to enhance ADCC compared to the original, unmodified antibody.

In some cases, LUCA19, SPL1, SG5 or LUCA40 binding can also activate both cellular and humoral immune responses and recruit more natural killer cells or increased production of cytokines (e.g., IL-2, IFN-g, IL-12, TNF-a, TNF-b, etc.) that further activate an individual's immune system to destroy cancerous cells. In yet another embodiment, LUCA19, SPL1, SG5 or LUCA40 can bind to cancerous cells, and macrophages or other phagocytic cell can opsonize the cancerous cells.

In some embodiments, the invention provides methods of conferring passive immunity comprising administering any of the compositions described herein.

The invention provides methods of delivering any of the compositions (including conjugates) described herein to an EphA2 expressing cell, such as an EphA2 expression cancer cells. These methods entail administering the compositions (including conjugates) described herein to an individual. In some embodiments, the methods provide for introducing, for example, a conjugate into a target cell. In yet another embodiment, LUCA19, SPL1, SG5 or LUCA40 can be conjugated to a therapeutic agent (such as a radioactive molecule, a toxin, e.g., saporin, calicheamicin, auristatin, or maytansinoid, or other chemotherapeutic molecule) or to liposomes or other vesicles containing chemotherapeutic compounds and administered to an individual to target these compounds to the cancer cell containing the antigen recognized by the antibody and thus eliminate cancerous cells. In yet another embodiment, the antibody can be employed as adjuvant therapy at the time of the surgical removal of a cancer expressing the antigen in order to delay the development of metastasis. The antibody can also be administered before surgery (neoadjuvant therapy) in a patient with a tumor expressing the antigen in order to decrease the size of the tumor and thus enable or simplify surgery, spare tissue during surgery, and/or decrease the resulting disfigurement.

Various formulations of LUCA19, SPL1, SG5 or LUCA40 and equivalent antibodies or fragments (e.g., Fab, Fab', F(ab')$_2$, Fv, Fc, etc.), such as chimeric antibodies, single chain (ScFv), mutants thereof, fusion proteins comprising an antibody portion, humanized antibodies, and any other modified configuration of LUCA19, SPL1, SG5 or LUCA40 that comprises an antigen EphA2 recognition site of the required specificity, may be used for administration. In some embodiments, LUCA19, SPL1, SG5 or LUCA40 antibodies or various formulations of LUCA19, SPL1, SG5 or LUCA40 thereof may be administered neat. In other embodiments, LUCA19, SPL1, SG5 or LUCA40 or various formulations of LUCA19, SPL1, SG5 or LUCA40 (including any composition embodiment described herein) thereof and a pharmaceutically acceptable excipient are administered, and may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington, The Science and Practice of Pharmacy* 20th Ed. Mack Publishing (2000).

Generally, these agents are formulated for administration by injection (e.g., intraperitoneally, intravenously, subcutaneously, intramuscularly, etc.), although other forms of administration (e.g., oral, mucosal, etc) can be also used. Accordingly, LUCA19, SPL1, SG5 or LUCA40 antibody and equivalents thereof are preferably combined with pharmaceutically acceptable vehicles such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 μg/kg body weight; at least about 500 μg/kg body weight; at least about 250 ug/kg body weight; at least about 100 μg/kg body weight; at least about 50 μg/kg body weight; at least about 10 ug/kg body weight; at least about 1 μg/kg body weight, or more, is administered. Empirical considerations, such as the half-life, generally will contribute to determination of the dosage. Antibodies that are compatible with the human immune system, such as humanized antibodies or fully human antibodies, may be used to prolong half-life of the antibody and to prevent the antibody being attacked by the host's immune system.

In some individuals, more than one dose may be required. Frequency of administration may be determined and adjusted over the course of therapy, and is based on reducing the number of cancerous cells, maintaining the reduction of cancerous cells, reducing the growth and/or proliferation of cancerous cells, or delaying the development of metastasis. The presence of cancerous cells can be identified by any number of methods known to one of skill in the art or discussed herein (e.g., detection by immunohistochemistry or flow cytometry of biopsies or biological samples). In some cases, sustained continuous release formulations of LUCA19, SPL1, SG5 or LUCA40 antibodies may be appropriate. Various formulations and devices for achieving sustained release are known in the art.

In one embodiment, dosages for LUCA19, SPL1, SG5 or LUCA40 antibodies may be determined empirically in individuals who have been given one or more administration(s). Individuals are given incremental dosages of LUCA19, SPL1, SG5 or LUCA40. To assess efficacy of LUCA19, SPL1, SG5 or LUCA40 or other equivalent antibody, markers of the specific cancer disease state can be monitored. These markers include: direct measurements of tumor size via palpation or visual observation; indirect measurement of tumor size by x-ray or other imaging techniques; an improvement as assessed by direct tumor biopsy and microscopic examination of the tumor sample; the measurement of an indirect tumor marker (e.g., PSA for prostate cancer), a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In some embodiments, more than one antibody may be present. The antibodies can be monoclonal or polyclonal. Such compositions may contain at least one, at least two, at least three, at least four, at least five different antibodies that are reactive against carcinomas, adenocarcinomas, sarcomas, or adenosarcomas. LUCA19, SPL1, SG5 or LUCA40 antibody can be admixed with one or more antibodies reactive against carcinomas, adenocarcinomas, sarcomas, or adenosarcomas in organs including but not limited to ovary, breast, lung, prostate, colon, kidney, skin, thyroid, bone, upper digestive tract, and pancreas. A mixture of antibodies, as they are often denoted in the art, may be particularly useful in treating a broader range of population of individuals.

Assessment of disease is performed using standard methods in the arts, such as imaging methods and monitoring appropriate marker(s).

Kits Comprising Antibodies and Polypeptides of the Invention that Bind to EphA2

The invention also provides kits comprising antibodies or any of the compositions described herein that bind to EphA2 for use in diagnosis and/or therapy. Accordingly, the kits comprise an antibody that can bind to EphA2 preferentially and/or form a complex with EphA2 (useful, for example, for detecting breast, colon, lung, or prostate cancerous cells). In some embodiments, the kits comprise anti-EphA2 antibody or an antibody that preferentially binds to the same epitope as LUCA19, SPL1, SG5 or LUCA40 preferentially binds. In some embodiments, the kits comprise anti-EphA2 antibody or an antibody that preferentially binds to the same epitope as LUCA19, SPL1, SG5 or LUCA40 preferentially binds linked to a therapeutic agent or a labeling agent. These kits may further include instruction and/or reagents for linking the antibody or any antibody or polypeptide embodiments described herein to the therapeutic agent(s) or the labeling agent(s). In some aspects, the binding of an antibody (e.g., monoclonal, polyclonal, human, humanized, etc.) to EphA2 is used for diagnosing cancer in an individual, for example, kits for detecting presence or absence of cancerous cells, and kits for detecting presence or absence of breast, colon, lung, or prostate cancerous cells. In other aspects, the kits may be used, for example, to treat an individual with cancer or a family history of cancer. Kits for treating individual with cancer include but not limited to kits for inhibiting growth and/or proliferation of cancer cells, for delivering a therapeutic agent to cancerous cells, for delivering a therapeutic agent into cancerous cells. The kits of this invention are in suitable packaging, and may optionally provide additional components such as, buffers and instructions for determining binding to EphA2, such as capture reagents, developing reagents, labels, reacting surfaces, means for detection, control samples, and interpretive information. The instructions may be for any measurement of antigen binding, including, but not limited to, those assays described herein. In other embodiments, the instructions may be for any of the methods described herein, including: instructions for inhibiting grow and/or proliferation of cancerous cells such as breast, lung, colon, or prostate, for delivering a therapeutic agent to cancerous cells, for delivering a therapeutic agent into cancerous cells. In some embodiments, reagents described above are supplied such that multiple measurements may be made, such as allowing for measurements in the same individual over time or multiple individuals. Any appropriate means for detecting binding of the antibodies may be employed (and provided in the kits) such as a labeled anti-human antibody, wherein the label may be an enzyme, fluorophore, chemiluminescent material radioisotope or coenzyme. Generally, the label used will be an enzyme.

The following examples are provided to illustrate, but not to limit, the invention.

EXAMPLES

Example 1

Preparation of Cancer Cell Lines as an Immunogen

Whole cells isolated from tissue or from cell culture were used as an immunogen for producing monoclonal antibodies that are specific for surface antigens representative of a particular cell type. Such methods, suitable for the practice of this invention, are described in U.S. Pat. No. 6,541,225. Generally, to produce monoclonal antibodies directed to cell-surface antigens of a specific cell type, it is desirable to immunize non-transformed B-cells with viable and intact cells of that type, preferably with those cells whose surfaces that are free of serum. Cell lines that are suitable for the generation of monoclonal antibodies against the antigen EphA2, such as but not limited to LUCA19, LUCA 40, or SPL1, include: BT-474 (ATCC #HTB-20), MDA-MB-175VII (ATCC #HB-25), MDA-MB-361 (ATCC #HB-27), SKBR3 (ATCC #HTB-30), SKMES-1 (ATCC #HTB-58), ES-2 (ATCC #CRL-1978), SKOV3 (ATCC #HTB-77), HPAFII (ATCC #CRL-1997), Hs700T (ATCC #HTB-147), Colo205 (ATCC #CCL-222), HT-29 (ATCC #HTB-38), SW480 (ATCC #CCL-228), SW948 (ATCC #CCL-237), A498 (ATCC #HTB-44) and Caki-2 (ATCC #HTB-47).

The cells were grown in the appropriate nutrient media supplemented with growth factors, but free of serum. Immunization with cells that have been propagated in a serum-supplemented medium can have extreme disadvantages. Serum contains a complex mixture of small and large biomolecules with undefined activities. These biomolecules can adhere to the surfaces of cells and thereby leading to the generation of antibodies cross-reacting with molecules not representative of the specific cell type. Additionally, binding of serum biomolecules to the cell surface may lead to the masking of desired cell surface antigen targets. A number of serum-free media preparations are commercially known and publicly available, such as for example, F12/DME (1:1) nutrient media with the following supplements: insulin (10 µg/ml final concentration), epidermal growth factor (EGF) (5 ng/ml final concentration), selenious acid ($2.5 \times 10^{-8}$ M final concentration), and porcine pituitary extract (PPE) (5 µl/ml final concentration).

To harvest the cells, the cell monolayers were rinsed once with calcium- and magnesium-free Hanks saline solution, incubated in 10 mM EDTA in Hanks saline solution at 37 C for 15 minutes. The cells were detached from the culture surface by gentle pipetting. The cell suspension was pelleted by centrifugation at 1000×g for 5 minutes. The supernatant was removed and cells were resuspended in serum-free medium with non-denaturing adjuvant as appropriate.

Example 2

Generation of Monoclonal Antibodies

A non-denaturing adjuvant (Ribi, R730, Corixa, Hamilton Mont.) was rehydrated to 2 ml in phosphate buffered saline. 100 µl of this rehydrated adjuvant was then gently mixed with some of the cell pellet from Example 1 to be used for immunization. Approximately $10^6$ cells per mouse were injected into Balb/c mice via footpad, approximately once or twice a week. The precise immunization schedule is as follows: Day zero, immunization plus Ribi. Day 3, immunization plus Ribi. Day 7, immunization plus Ribi. Day 24, immunization minus Ribi. Day 29, immunization minus Ribi. Day 32, immunization minus Ribi. Day 36, immunization minus Ribi. Day 44, immunization minus Ribi. Day 51, immunization minus Ribi. Day 69, bleed for titer test. Day 71. immunization plus Ribi. Day 74, immunization plus Ribi. Day 81, immunization plus Ribi. Day 91, pre-fusion boost (no Ribi). Day 104, harvest nodes for fusion.

At Day 69, a drop of blood was drawn from the tail of each immunized animal to test the titer of antibodies against the cell line used to immunize using FACS analysis. When the titer reached at least 1:2000, the mice were sacrificed using $CO_2$ followed by cervical dislocation. Lymph nodes were harvested for hybridoma preparation.

Lymphocytes from mice were fused with the mouse myeloma line X63-Ag8.653 using 35% polyethylene glycol 4000. On day 10 following the fusion, the hybridoma supernatants were screened for the presence of the immunizing cells-specific monoclonal antibodies by fluorescence activated cell sorting (FACS). Conditioned medium from each hybridoma was incubated for 30 minutes with an aliquot of human fetal kidney cells. After incubation, the cell samples were washed, resuspended in 0.1 ml diluent and incubated with 1 µg/ml of FITC conjugated F(ab')2 fragment of goat anti-mouse IgG for 30 min at 4° C. The cells were washed, resuspended in 0.2 ml FACS diluent and analyzed using a FACScan cell analyzer (Becton Dickinson; San Jose, Calif.). Hybridoma clones were selected for further expansion, cloning, and characterization based on their binding to the surface of the human fetal kidney cells by FACS. A hybridoma making a monoclonal antibody designated mu-SPL1 which binds an antigen designated Ag-SPL1 and an epitope on that antigen designated Ag-SPL1.1 was selected. A hybridoma making monoclonal antibody designated mu-LUCA19 which binds an antigen designated Ag-LUCA19 and an epitope on that antigen designated Ag-LUCA19.1 was selected. A hybridoma making monoclonal antibody designated mu-LUCA40 that binds an antigen designated Ag-LUCA40 and an epitope on that antigen designated Ag-LUCA40.1. A hybridoma making monoclonal antibody designated mu-SG5 that binds an antigen designated Ag-SG5 and an epitope on that antigen designated Ag-SG5.1. The hybridomas that produce the monoclonal antibodies, mu-SPL-1, mu-LUCA19, mu-LUCA40 and mu-SG5 were expanded in culture for purification of the monoclonal antibodies in a culture medium that is able to support monoclonal antibody growth and antibody purification.

Example 3

Purification of Anti-EphA2 Antibodies

Human cancer cells such as but not limited to SKMES-1, 786-O, and Colo205 cell lines were detached from tissue culture flasks in the presence of 10.0 mM EDTA, centrifuged at 1400 rpm for 5 minutes and resuspended in PBS containing 1% BSA and 2 mM EDTA (FACS diluent). The cells were counted and adjusted to $10^7$ cells/ml. About 0.1 ml of cells were incubated with 100 µl FACS diluent for 30 minutes at 37° C. Monoclonal antibodies that bind to the human cancer cell lines were purified from tissue culture supernatant using protein-G affinity chromatography. If needed the tissue culture supernatant may be passed over a bovine IgG column before antibody purification in order to remove excess bovine IgG. The following materials were used for the antibody purification process: hybridoma tissue culture supernatant, Immunopure (G) IgG binding buffer (Pierce #21011 Rockford, Ill.), Immunopure IgG Elution Buffer (Pierce #21009), concentrated HCl (for adjusting pH), Corning 1 liter PES (polyether sulfone), 0.22 µm filter (Corning #431098, Corning, N.Y.), Amersham Pharmacia AKTA Explorer System (Amersham Biosciences, Piscataway, N.J.), Protein-G Sepharose 4 Fast Flow (Amersham Biosciences #17-0618-03), Stripping buffer consisting of 3M Potassium thiocyanate/50 mM Tris pH 7.8, and PBS (phosphate buffered saline), 3M Tris pH 9.0.

To purify the mouse anti-human SPL1, mouse anti-human LUCA19 and mouse anti-human LUCA40 antibodies referred to herein as mu-SPL1, mu-LUCA19 and mu-LUCA40, respectively, the volume of the supernatant was measured and an equal volume of binding buffer was added to the supernatant. The mixture was allowed to equilibrate to room temperature. The supernatant was clarified by passage through a 0.22 µM filter. The supernatant was loaded onto a protein-G Sepharose column using the AKTA Explorer system (Amersham Biosciences) and then washed with 5-10 column volumes of binding buffer. The monoclonal antibody was eluted with the elution buffer, and fractions were collected. The fractions were neutralized upon elution with the addition of 3M Tris, pH 9.0 to empty tubes (1/60 volume of the fractions). The peak fractions containing the monoclonal antibody were pooled. The pooled samples was injected into a pre-wetted slidealyzer cassette (10,000 MW cutoff; Pierce #66810) and dialyzed in 1× PBS at 4° C. (with 3 buffer changes of at least 4 hours of dialysis per change). The purified monoclonal antibody was sterile filtered (0.2 µm Acrodisc) and stored at 2-8° C.

A sample of purified antibody is taken for determination of concentration by UV absorbance ($A_{280}$) and SDS-Polyacrylamide gel electrophoresis (SDS-PAGE). SDS-PAGE is run under both non-reducing and reducing conditions for analysis of molecular weight, identification of the typical banding pattern of monoclonal antibodies and assessment of purity.

After purification of the mu-SPL1, mu-LUCA19 and mu-LUCA40 monoclonal antibody from the hybridoma supernatant, it was re-tested for binding to respective immunizing or target cells of interest. The cell samples were prepared as described above and incubated with the purified antibody at various concentrations. After incubation the cells were washed, resuspended in 0.1 ml diluent and incubated with 1 µg of FITC conjugated F(ab)'2 fragment of goat anti-mouse IgG for 30 minutes at 4° C. The cells were washed, resuspended in 0.5 ml FACS diluent and analyzed using a FACScan cell sorter (Becton Dickinson, San Jose, Calif.). A shift to the right on the FACScan histogram indicated that the purified antibody still bound to the cells.

In other experiments, the binding of the mu-SPL1, mu-LUCA19 and mu-LUCA40 antibodies to SPL1, LUCA19 and LUCA40, respectively, was tested and confirmed using live cell ELISA. the following method was used, although other methods commonly known in the field are applicable. Cells (HT-29, SKOV3, SKMES-1, SW480, SKBR-3, and HPAFII) were grown in 10% fetal bovine serum (FBS) containing media to confluency on tissue culture treated 96-well plates (Falcon). Cells were washed with PBS and then incubated with 50 µl of desired antibodies at a desired concentration in Hank's Balanced Salt Solution (HBSS) containing 1% BSA and 0.1% sodium azide for 1 hour at room temperature. The cells were then washed three times with 100 µl per well of HBSS before incubation with horseradish peroxidase (HRP) secondary antibody (50 µl per well diluted in HBSS) for 30 minutes at room temperature. The cells were finally washed three times with HBSS and the color change substrate (TMB substrate, KPL) was added to each well at 100 µl per well. The color change reaction was stopped with the addition of 100 µl per well of 1M phosphoric acid. The plates were then read at O.D. 450 nm.

Example 4

Western Blot Analysis of SPL1, LUCA19 and LLICA40 Expression in Cancer Cell Line SW480

Renal cell carcinoma cell line SW480 (ATCC #CCL-228) were grown to confluency on 175 $cm^2$ culture dishes. The confluent monolayer was washed three times with Hank's Balanced Salt Solution (HBSS+ containing no sodium bicarbonate or phenol red; buffered with 10 mM HEPES, pH 7.4; Sigma Chemicals) and biotinylated with 200 µg of sulfo-NHS-LC-biotin (Pierce Endogen) for 30 minutes at room temperature. The cells were then washed with HBSS+ containing 0.1M Tris, pH 7.4 (Sigma Chemicals) and incubated in HBSS+ containing 0.1M Tris, pH 7.4 for 15 minutes at room temperature. The cells were finally washed three times with HBSS+ and lysed by incubation for 5 minutes, on ice, in lysis buffer (HBSS+ with 2% Triton X-100, 2 mM PMSF, 0.1% sodium azide, and 1 tablet per 5 ml lysis buffer of EDTA free complete mini-protease cocktail (Roche Molecular Biochemicals)).

Cells were scraped in lysis buffer and lysates collected. Lysates were centrifuged at 14,000-xg for one hour at 4° C. The clarified lysate was then pre-cleared for 2 hours at 4° C. with 5 µl of human IgG conjugated (1mg/ml) CNBr 4MB sepharose beads (Amersham Pharmacia). Human IgG beads were centrifuged and removed, and then the pre-cleared lysate was then incubated with monoclonal antibody mu-SPL1, mu-LUCA19, mu-SG5 or mu-LUCA40 conjugated to CNBr 4MB Sepharose beads (conjugated at 1 mg/ml) for 2 hours at 4° C. The mu-SPL1, mu-LUCA19, mu-SG5 or mu-LUCA40 beads were centrifuged and removed after the 2-hour incubation. Both the human IgG and the mu-SPL1, mu-LUCA19, mu-SG5 or mu-LUCA40 beads were individually washed three times with 1 ml of lysis buffer and then washed three times with 1 ml HBSS+. The washed beads were eluted by the addition of 30 µl of SDS-PAGE sample buffer and boiling at 99° C. for 5 minutes.

The samples were then resolved on a 4-20% Novex gradient gel (Invitrogen), and transferred onto 0.2 µm nitrocellulose membrane (Invitrogen) and visualized by horse radish peroxidase (HRP) conjugated streptavidin (Pierce Endogen) or western blotted with 5 µg/blot of mu-SPL1, mu-LUCA19, mu-SG5 or mu-LUCA40.

For detection with HRP conjugated streptavidin, the nitrocellulose was first blocked for 1 hour with blocking buffer (5% non-fat dry milk in Tris-buffered saline with 0.05% Tween-20 (TBST)). HRP conjugated streptavidin was diluted into TBST at 1 µg/ml and exposed to the nitrocellulose for 30 minutes at room temperature. The nitrocellulose was washed three times in TBST before visualization with ECL+ (Amersham).

For western blotting with mu-SPL1, mu-LUCA19, mu-SG5 or mu-LUCA40, the nitrocellulose was similarly blocked for 1 hour in blocking buffer. The nitrocellulose was then incubated in a heat sealed plastic pouch containing 1 ml of 5 µg/ml mu-SPL1, mu-LUCA19, mu-SG5 or mu-LUCA40 diluted in blocking buffer. The nitrocellulose was washed 3 times with TBST before incubation with 10 ml of 1 µg/ml HRP conjugated donkey anti-mouse IgG (heavy and light chain specific, cross adsorbed against bovine, chicken, goat, guinea pig, Syrian hamsters, horse, human, rabbit, sheep serum proteins; Jackson Immunoresearch Cat. #709-035-149) for 1 hour at room temperature. The nitrocellulose was finally washed three times with TBST and visualized by ECL+ (Amersham).

Example 5

Immunohistochemistry Methods

Frozen tissue samples from cancer patients were embedded in OCT compound and quick-frozen in isopentane with dry ice. Cryosections were cut with a Leica 3050 CM microtome at thickness of 8-10 µm and thaw-mounted on SuperFrost Plus slides (VWR #48311-703). The sections were fixed with 75% acetone/25% ethanol at 10° C. and allowed to air-dry 2-4 hours at room temperature. The fixed sections were stored at −80° C. until use.

For immunohistochemistry, the tissue sections were retrieved washed in Tris buffered 0.05% Tween (TB-T) and blocked in blocking buffer (TB-T, 5% normal goat serum and 100 µg/ml avidin) for 30 minutes at room temperature. The slides were then incubated with the mu-LUCA19, mu-LUCA40, mu-SG5 or mu-SPL1 and control monoclonal antibodies diluted in blocking buffer (1 µg/ml) for 60-90 minutes at room temperature. The sections were then washed three times with the blocking buffer. The bound monoclonal antibodies were detected with a goat anti-mouse IgG+IgM (H+L) F(ab')$_2$-peroxidase conjugates and the peroxidase substrate diaminobenzidine (1 mg/ml, Sigma cat. No. D 5637) in 0.1 M sodium acetate buffer pH 5.05 and 0.003% hydrogen peroxide (Sigma cat. No. H1009). The stained slides were counter-stained with hematoxylin and examined under Nikon microscope.

In some cases, paraffin embedded formaldehyde-fixed tissues may be used for immunohistochemistry after appropriate antigen retrieval methods were employed. One such antigen retrieval method is described in Mangham and Isaacson, *Histopathology* 35:129-33 (1999). Other methods of antigen retrieval and/or detection may be used by one skilled in the art. Results from similar experiments performed using frozen tissues or, where appropriate, fixed tissue with antigen retrieval and polyMICA detection were performed. The binding of anti-LUCA19, anti-LUCA40 and anti-SPL1 antibodies to a variety of normal and cancer tissues was assessed. In all cases, antibody binding in control fixed tissues was correlated with that of frozen tissues. The results from frozen tissues were only used if the two did not match in the controls.

For convenience, a summary of the combined results of several experiments using frozen surgical tissue from different sources is shown below in Tables 1-7. Tables 1-4 summarize the distribution of LUCA19, LUCA40, SPL1, and SG5 antigens on normal human tissues. Tables 5-7 summarize the distribution of LUCA19, LUCA40 and SPL1 antigens on various human tumor tissues.

TABLE 1

Distribution of LUCA19 antigen in normal human tissues

| Tissue Type | Results |
|---|---|
| Skin | Negative |
| Lung | Negative |
| Kidney | Negative |
| Pancreas | Negative except for 1+ staining on a few ducts |
| Liver | Negative |
| Colon | Negative |
| Duodenum | 1+ staining in basal epithelium |

TABLE 2

Distribution of LUCA40 antigen in normal human tissues

| Tissue Type | Results |
| --- | --- |
| Skin | Negative except +/− on a few small subcutaneous vessels |
| Lung | Negative |
| Kidney | Negative except for +/− on glomeruli |
| Pancreas | Negative |
| Liver | Negative except for +/− on parenchyma |
| Colon | Negative except +/− over mucosa and muscularis |
| Duodenum | Negative |
| Prostate | Negative |
| Ovary | Negative |
| Breast | Negative except +/− over glandular structures |

TABLE 3

Distribution of SPL1 antigen in normal human tissues

| Tissue Type | Results |
| --- | --- |
| Skin | Negative |
| Lung | Negative |
| Kidney | Negative |
| Pancreas | Negative |
| Liver | Negative |
| Colon | 1+ focal staining on mucosa (50%) |
| Duodenum | 1+ mucosal staining |
| Prostate | Negative |
| Ovary | Negative |
| Breast | Negative |

TABLE 4

Distribution of SG5 antigen in normal human tissues

| Tissue Type | Results |
| --- | --- |
| Skin | +/− staining on epidermis and sweat glands |
| Lung | Negative |
| Kidney | Negative |
| Pancreas | Negative |
| Liver | +/− staining (parenchymal hue) |
| Colon | Negative |
| Stomach | Negative |
| Prostate | Negative |
| Ovary | Negative |
| Breast | Negative |

TABLE 5

Distribution of LUCA19 antigen in human tumor tissues

| Tissue Type | Results |
| --- | --- |
| Prostate | Negative on 4/4 tumors screened |
| Colon | 1-3+ staining on 5/5 tumors screened |
| Kidney | Negative on 5/5 tumors screened |
| Lung | 1-2+ staining on 4/7 tumors screened and negative on 3/7 tumors screened |
| Ovary | Negative on 4/4 tumors screened |
| Pancreas | 2-3+ on 5/5 tumors screened |
| Breast | Variable; 1-2+ on 1/3 tumors screened |

TABLE 6

Distribution of LUCA40 antigen in human tumor tissues

| Tissue Type | Results |
| --- | --- |
| Prostate | Variable; Negative to 1+ staining; 8 tumors screened |
| Colon | 1-3+ staining on 8/8 tumors screened |
| Kidney | +/− stromal staining on 5/5 tumors screened |
| Lung | Variable; Negative to 1+ staining; 8 tumors screened |
| Ovary | +/− stromal staining on 5/5 tumors screened |
| Pancreas | 1-2+ staining on 7/7 tumors screened |
| Breast | Negative on 3/4 tumors screened; +/− on 1/4 tumors screened |

TABLE 7

Distribution of SPL1 antigen in human tumor tissues

| Tissue Type | Results |
| --- | --- |
| Prostate | Negative on 6/6 tumors screened |
| Colon | 1-3+ apical staining on 7/9 tumors; Negative on 2/9 tumors screened |
| Kidney | Negative on 5/5 tumors screened |
| Lung | Variable +/− to 1+ staining on 3/8 tumors screened; Negative on 5/8 tumors screened |
| Ovary | Negative on 5/5 tumors screened |
| Pancreas | 1-2+ on 6/6 tumors screened |
| Breast | Negative on 4/4 tumors screened |

Example 6

Immunocytochemistry Results

Monoclonal antibodies mu-LUCA19, mu-LUCA40 and mu-SPL1 were used to test reactivity with various cell lines from different types of tissues. The results were scored as '+' for weak positive staining, '++' for moderate positive staining, '+++' for strong positive staining and '−' for negative staining.

Immunohistochemistry results were obtained using CellArray™ technology, as described in WO 01/43869. Cells from different established cell lines were removed from the growth surface without using proteases, packed and embedded in OCT compound. The cells were frozen and sectioned, then stained using a standard IHC protocol.

Results of the binding of the mu-LUCA19, mu-LUCA40 and mu-SPL1 antibodies to various established human normal and tumor cell lines are compiled for convenience in Tables 8-10. The experiments represented in Table 8 include Live-cell ELISA, Sarcoma Array and CellArray™ binding experiments with mu-LUCA19 using the methods described herein. The experiments represented in Table 9 include Live-cell ELISA, Sarcoma Array and Cell Array™ binding experiments with mu-LUCA40 using the methods described herein. The experiments represented in Table 10 include Live-cell ELISA, Sarcoma Array and Cell Array™ binding experiments with mu-SPL1 using the methods described herein.

TABLE 8

| | | | | Mu-LUCA19 binding | | |
|---|---|---|---|---|---|---|
| Cell line | ATCC# | Organ | Cell Type | Reactivity Cell Array | Reactivity Sarcoma Array | Reactivity Live Cell ELISA |
| MDA361 | HB-27 | Breast | Adenocarcinoma | − | | |
| MDA175 | HB-29 | Breast | Ductal carcinoma | − | | |
| MCF7 | HTB-22 | Breast | Adenocarcinoma | − | | |
| SKBR3 | HTB-30 | Breast | Metastatic; pleural effusion adenocarcinoma | − | | − |
| BT474 | HTB-20 | Breast | Ductal carcinoma | − | | |
| HUVEC | Primary | Endothelial Cell | Normal human adult | ++ | | |
| HMEC | CC-2251* | Breast | Normal mammary epithelial | − | | |
| SKOV3 | HTB-77 | Ovary | Adenocarcinoma | ++ | | +++ |
| ES-2 | CRL-1978 | Ovary | Carcinoma | + | | |
| SKMES1 | HTB-58 | Lung | Squamous carcinoma | − | | + |
| CA130 | RAVEN | Lung | Small cell carcinoma | +/− | | |
| A549 | CCL-185 | Lung | Carcinoma | + | | |
| 9979 | RAVEN | Lung | Lung cancer cell line | − | | |
| SW948 | CCL-237 | Colon | Colorectal adenocarcinoma | − | | |
| SW480 | CCL-228 | Colon | Colorectal adenocarcinoma | − | | +++ |
| HT-29 | HTB-38 | Colon | Colorectal adenocarcinoma | − | | + |
| Colo205 | CCL-222 | Colon | Ascites colorectal adenocarcinoma | +/− | | |
| Hs700T | HTB-147 | Pancreas | Adenocarcinoma | − | | |
| HPAFII | CRL-1997 | Pancreas | Adenocarcinoma | ++ | | − |
| AsPC-1 | CRL-1682 | Pancreas | Adenocarcinoma | + | | |
| 9926 | RAVEN | Pancreas | Adenocarcinoma | ++ | | |
| SVT2 | CCL-163.1 | Embryo (Mouse) | Fibroblast; SV40 transformed | − | | |
| Cos7 | CRL-1651 | Kidney (African Green Monkey) | SV40 transformed | +/− | | |
| RL65 | CRL-10354 | Lung (Rat) | Epithelial cell | − | | |
| Calu3 | HTB-55 | Lung | Adenocarcinoma | +++ | | |
| Caki2 | HTB-47 | Kidney | Clear cell carcinoma | + | | |
| A498 | HTB-44 | Kidney | Carcinoma | +/− | | |
| 786-O | CRL-1932 | Kidney | Renal cell carcinoma | +/− | | |
| 293 | CRL-1573 | Kidney | Transformed with adenovirus5 DNA | − | | |
| TDH | RAVEN | Prostate | Prostate cancer cell line | − | | |
| PC3 | CRL-1435 | Prostate | Adenocarcinoma | − | | |
| LNCaP | CRL-1740 | Prostate | Carcinoma | − | | |
| DU145 | HTB-81 | Prostate | Adenocarcinoma | +++ | | |
| 22RV1 | CRL-2505 | Prostate | Carcinoma | − | | |
| Hs746T | HTB-135 | Stomach | Carcinoma | ++ | | |
| N87 | CRL-5822 | Stomach | Metastatic; liver gastric carcinoma | ++ | | |
| SW872 | HTB-92 | Connective Tissue | Liposarcoma | | ++ | |
| SW684 | HTB-91 | Connective Tissue | Fibrosarcoma | | ++ | |
| SK-UT-1 | HTB-114 | Uterus | Leiomyosarcoma | | ++ | |
| SK-LMS-1 | HTB-88 | Vulva | Leiomyosarcoma | | ++ | |
| SK-ES-1 | HTB-86 | Bone | Ewing's sarcoma | | − | |
| RD-ES | HTB-166 | Bone | Ewing's sarcoma | | +/− | |
| RD | CCL-136 | Muscle | Rhabdomyosarcoma | | − | |
| MG-63 | CRL-1427 | Bone | Osteosarcoma | | − | |
| HT-1080 | CCL-121 | Connective Tissue | Fibrosarcoma | | ++ | |
| G-292 | CRL-1423 | Bone | Osteosarcoma | | − | |
| A-204 | HTB-82 | Muscle | Rhabdomyosarcoma | | + | |

*CC-2251 BioWhittaker

TABLE 9

| | | | | Reactivity Cell Array | Reactivity Sarcoma Array | Reactivity Live Cell ELISA |
|---|---|---|---|---|---|---|
| Cell line | ATCC# | Organ | Cell Type | | | |
| HMEC | CC-2251* | Breast | Normal mammary epithelial | − | | |
| HUVEC | Primary | Endothelial Cell | Normal human adult | ++ | | |
| BT474 | HTB-20 | Breast | Ductal carcinoma | − | | |
| MCF7 | HTB-22 | Breast | Adenocarcinoma | − | | |
| MDA175 | HB-29 | Breast | Ductal carcinoma | − | | |
| MDA361 | HB-27 | Breast | Adenocarcinoma | − | | |
| SKBR3 | HTB-30 | Breast | Metastatic; pleural effusion adenocarcinoma | − | | − |
| 9979 | RAVEN | Lung | Lung cancer cell line | + | | |
| A549 | CCL-185 | Lung | Carcinoma | + | | |
| CA130 | RAVEN | Lung | Small cell carcinoma | + | | |
| Calu3 | HTB-55 | Lung | Adenocarcinoma | + | | |
| SKMES1 | HTB-58 | Lung | Squamous carcinoma | − | | + |
| ES-2 | CRL-1978 | Ovary | Carcinoma | +++ | | |
| SKOV3 | HTB-77 | Ovary | Adenocarcinoma | + | | +++ |
| 9926 | RAVEN | Pancreas | Adenocarcinoma | ++ | | |
| AsPC-1 | CRL-1682 | Pancreas | Adenocarcinoma | + | | |
| HPAFII | CRL-1997 | Pancreas | Adenocarcinoma | ++ | | − |
| Hs700T | HTB-147 | Pancreas | Adenocarcinoma | + | | |
| Colo205 | CCL-222 | Colon | Ascites colorectal adenocarcinoma | + | | |
| HT-29 | HTB-38 | Colon | Colorectal adenocarcinoma | − | | + |
| SW480 | CCL-228 | Colon | Colorectal adenocarcinoma | ++ | | +++ |
| SW948 | CCL-237 | Colon | Colorectal adenocarcinoma | − | | |
| 293 | CRL-1573 | Kidney | Transformed with adenovirus5 DNA | +/− | | |
| 786-O | CRL-1932 | Kidney | Renal cell carcinoma | + | | |
| A498 | HTB-44 | Kidney | Carcinoma | + | | |
| Caki2 | HTB-47 | Kidney | Clear cell carcinoma | + | | |
| Cos7 | CRL-1651 | Kidney (African Green Monkey) | SV40 transformed | ++ | | |
| RL65 | CRL-10354 | Lung (Rat) | Epithelial cell | − | | |
| SVT2 | CCL-163.1 | Embryo (Mouse) | Fibroblast; SV40 transformed | − | | |
| 22RV1 | CRL-2505 | Prostate | Carcinoma | − | | |
| DU145 | HTB-81 | Prostate | Adenocarcinoma | − | | |
| LNCaP | CRL-1740 | Prostate | Carcinoma | − | | |
| PC3 | CRL-1435 | Prostate | Adenocarcinoma | − | | |
| TDH | RAVEN | Prostate | Prostate cancer cell line | ++ | | |
| Hs746T | HTB-135 | Stomach | Carcinoma | + | | |
| N87 | CRL-5822 | Stomach | Metastatic; liver gastric carcinoma | ++ | | |
| SW872 | HTB-92 | Connective Tissue | Liposarcoma | | ++ | |
| SW684 | HTB-91 | Connective Tissue | Fibrosarcoma | | ++ | |
| SK-UT-1 | HTB-114 | Uterus | Leiomyosarcoma | | + | |
| SK-LMS-1 | HTB-88 | Vulva | Leiomyosarcoma | | ++ | |
| SK-ES-1 | HTB-86 | Bone | Ewing's sarcoma | | − | |
| RD-ES | HTB-166 | Bone | Ewing's sarcoma | | +/− | |
| RD | CCL-136 | Muscle | Rhabdomyosarcoma | | − | |
| MG-63 | CRL-1427 | Bone | Osteosarcoma | | − | |
| HT-1080 | CCL-121 | Connective Tissue | Fibrosarcoma | | ++ | |
| G-292 | CRL-1423 | Bone | Osteosarcoma | | − | |
| A204 | HTB-82 | Muscle | Rhabdomyosarcoma | | + | |

*CC-2251 BioWhittaker

TABLE 10

| Cell line | ATCC# | Organ | Cell Type | Reactivity Cell Array | Reactivity Sarcoma Array | Reactivity Live Cell ELISA |
|---|---|---|---|---|---|---|
| HMEC | CC-2251* | Breast | Normal mammary epithelial | − | | |
| HUVEC | Primary | Endothelial Cell | Normal human adult | ++ | | |
| BT474 | HTB-20 | Breast | Ductal carcinoma | − | | |
| MCF7 | HTB-22 | Breast | Adenocarcinoma | − | | |
| MDA175 | HB-29 | Breast | Ductal carcinoma | − | | |
| MDA361 | HB-27 | Breast | Adenocarcinoma | − | | |
| SKBR3 | HTB-30 | Breast | Metastatic; pleural effusion adenocarcinoma | − | | − |
| 9979 | RAVEN | Lung | Lung cancer cell line | + | | |
| A549 | CCL-185 | Lung | Carcinoma | + | | |
| CA130 | RAVEN | Lung | Small cell carcinoma | + | | |
| Calu3 | HTB-55 | Lung | Adenocarcinoma | + | | |
| SKMES1 | HTB-58 | Lung | Squamous carcinoma | − | | + |
| ES-2 | CRL-1978 | Ovary | Carcinoma | +++ | | |
| SKOV3 | HTB-77 | Ovary | Adenocarcinoma | ++ | | +++ |
| 9926 | RAVEN | Pancreas | Adenocarcinoma | ++ | | |
| AsPC-1 | CRL-1682 | Pancreas | Adenocarcinoma | ++ | | |
| HPAFII | CRL-1997 | Pancreas | Adenocarcinoma | ++ (75%) | | − |
| Hs700T | HTB-147 | Pancreas | Adenocarcinoma | +/− | | |
| Colo205 | CCL-222 | Colon | Ascites colorectal adenocarcinoma | +/− | | |
| HT-29 | HTB-38 | Colon | Colorectal adenocarcinoma | +/− | | + |
| SW480 | CCL-228 | Colon | Colorectal adenocarcinoma | ++ | | +++ |
| SW948 | CCL-237 | Colon | Colorectal adenocarcinoma | + | | |
| 293 | CRL-1573 | Kidney | Transformed with adenovirus5 DNA | +/− | | |
| 786-O | CRL-1932 | Kidney | Renal cell carcinoma | + | | |
| A498 | HTB-44 | Kidney | Carcinoma | + | | |
| Caki2 | HTB-47 | Kidney | Clear cell carcinoma | ++ | | |
| Cos7 | CRL-1651 | Kidney (African Green Monkey) | SV40 transformed | ++ | | |
| RL65 | CRL-10354 | Lung (Rat) | Epithelial cell | − | | |
| SVT2 | CCL-163.1 | Embryo (Mouse) | Fibroblast; SV40 transformed | − | | |
| 22RV1 | CRL-2505 | Prostate | Carcinoma | − | | |
| DU145 | HTB-81 | Prostate | Adenocarcinoma | +/− | | |
| LNCaP | CRL-1740 | Prostate | Carcinoma | − | | |
| PC3 | CRL-1435 | Prostate | Adenocarcinoma | − | | |
| TDH | RAVEN | Prostate | Prostate cancer cell line | ++ | | |
| Hs746T | HTB-135 | Stomach | Carcinoma | + | | |
| N87 | CRL-5822 | Stomach | Metastatic; liver gastric carcinoma | ++ | | |
| SW872 | HTB-92 | Connective Tissue | Liposarcoma | | + | |
| SW684 | HTB-91 | Connective Tissue | Fibrosarcoma | | ++ | |
| SK-UT-1 | HTB-114 | Uterus | Leiomyosarcoma | | + | |
| SK-LMS-1 | HTB-88 | Vulva | Leiomyosarcoma | | ++ | |
| SK-ES-1 | HTB-86 | Bone | Ewing's sarcoma | | − | |
| RD-ES | HTB-166 | Bone | Ewing's sarcoma | | − | |
| RD | CCL-136 | Muscle | Rhabdomyosarcoma | | − | |
| MG-63 | CRL-1427 | Bone | Osteosarcoma | | − | |
| HT-1080 | CCL-121 | Connective Tissue | Fibrosarcoma | | ++ | |
| G-292 | CRL-1423 | Bone | Osteosarcoma | | − | |
| A204 | HTB-82 | Muscle | Rhabdomyosarcoma | | + | |

*CC-2251 BioWhitaker

Results of the binding of the mu-LUCA19, mu-LUCA40 and mu-SPL1 antibodies to various established tumor cell lines from the National Cancer Institute (NCI) are compiled for convenience in Table 11 using the methods described herein.

TABLE 11

| | NCI Cell Line Array | | | | |
|---|---|---|---|---|---|
| Cell Line | Tumor Origin | Histologic Type | LUCA19 Reactivity | LUCA40 Reactivity | SPL1 Reactivity |
| CRF-CEM | Peripheral blood | Acute lymphoblastic leukemia | − | − | − |
| HL-60(TB) | | Procyelocytic leukemia | − | − | − |
| K-562 | Pleural effusion | Chronic myelogenous leukemia | − | − | − |
| MOLT-4 | Peripheral blood | Acute lymphoblastic leukemia | − | − | − |
| RPMI-8226 | Peripheral blood | Multiple myeloma | − | − | − |
| SR | | Immunoblastic large cell lymphoma | − | − | − |
| A549 | Lung | Carcinoma | + | + | + |
| EKVX | Lung | Adenocarcinoma | − | − | − |
| HOP-62 | Lung | Adenocarcinoma | +++ | +++ | +++ |
| HOP-92 | Lung | Large cell, undifferentiated | + | + | ++ |
| NCI-H226 | Lung | Squamous cell | + | ++ | ++ |
| NCI-H23 | Lung | Adenocarcinoma | +/− | − | + |
| NCI-H322M | Lung | Bronchi alveolar carcinoma | − | − | − |
| NCI-H460 | Lung | Non-small cell | − | − | − |
| NCI-H522 | Lung | Adenocarcinoma | ++ | ++ | ++ |
| Colo205 | Colon | Ascites colorectal adenocarcinoma | +/− | +/− | + (50%) |
| HCC-2998 | Colon | Carcinoma | ++ | ++ | +++ |
| HCT-116 | Colon | Carcinoma | ++ | ++ | ++ |
| HCT-15 | Colon | Adenocarcinoma | + | +/− | + |
| HT29 | Colon | Colorectal adenocarcinoma | − | − | + |
| KM12 | Colon | Adenocarcinoma | + | ++ | ++ |
| SW-620 | Colorectal adenocarcinoma | Metastatic; lymph node | ++ | ++ | +++ |
| SF-268 | CNS | Anaplastic astrocytoma | ++ | ++ | ++ |
| SF-295 | CNS | Glioblastoma multiform | + | + | + |
| SF-539 | CNS | Gliosarcoma | ++ | ++ | ++ |
| SNB-19 | CNS | Glioblastoma | ++ | ++ | ++ |
| SNB-75 | CNS | Astrocytoma | +/− | +/− | +/− |
| U251 | CNS | Glioblastoma | +++ | ++ | ++ |
| LOX IMVI | Lymph node metastasis | Malignant amelanotic melanoma | + | + | ++ |
| MALME-3M | Lung metastasis | Malignant melanoma | − | − | + |
| M14 | | Amelanotic melanoma | − | − | − |
| SK-MEL-2 | Skin metastasis-thigh | Malignant melanoma | − | − | − |
| SK-MEL-28 | | Malignant melanoma | − | − | − |
| SK-MEL-5 | Axcillary node metastasis | Malignant melanoma | − | − | − |
| UACC--257 | | Malignant melanoma | + | + | + |
| UACC-62 | | Malignant melanoma | − | − | − |
| IGR-OV1 | Ovary | Cystoadenocarcinoma | − | − | − |
| OVCAR-3 | Ovary | Adenocarcinoma | ++ | ++ (75%) | ++ |
| OVCAR-4 | Ovary | Adenocarcinoma | + | + | + |
| OVCAR-5 | Ovary | Adenocarcinoma | +++ | ++ | +++ |
| OVCAR-8 | Ovary | Adenocarcinoma | +++ | + | ++ |
| SKOV3 | Ovary | Adenocarcinoma | ++ | + | + |
| PC3 | Prostate | Adenocarcinoma | − | − | − |
| DU145 | Prostate | Adenocarcinoma | − | − | − |
| 786-O | Kidney | Renal cell carcinoma | +/− | + | + |
| A498 | Kidney | Carcinoma | +/− | + | + |
| ACHN | Kidney | Carcinoma | +++ | ++ | ++ |
| CAKI-1 | Kidney | Adenocarcinoma | ++ | ++ | ++ |
| SN12C | Kidney | Carcinoma | ++ | ++ | +++ |
| TK-10 | Kidney | Carcinoma | + | + | + |
| UO-31 | Kidney | Carcinoma | ++ | ++ | ++ |
| MCF-7 | Breast | Adenocarcinoma | − | − | − |
| NCI-ADR-RES | Breast | Metastatic; Pleural | + | + | ++ |

TABLE 11-continued

NCI Cell Line Array

| Cell Line | Tumor Origin | Histologic Type | LUCA19 Reactivity | LUCA40 Reactivity | SPL1 Reactivity |
|---|---|---|---|---|---|
| MDA-MB-231 | Breast | effusion adenocarcinoma Metastatic; Pleural effusion adenocarcinoma | ++ | ++ | +++ |
| Hs 578T | Breast | Ductal carcinoma | + | +/− | + |
| MDA-MB-435 | Breast | Metastatic; Pleural effusion adenocarcinoma | − | − | − |
| BT-549 | Breast | Metastatic; Lymph node; Inflitrating ductal carcinoma | +++ | +++ | +++ |
| T-47D | Breast | Metastatic; Pleural effusion; Ductal carcinoma | − | − | − |

Monoclonal antibodies mu-LUCA19, mu-LUCA40 and mu-SPL1 were used to test reactivity with glioma-derived cell lines. Immunocytochemistry results were obtained using similar protocols as described above for the CellArray™ technology. The glioma-derived cell lines were removed from the growth surface without using proteases, packed and embedded in OCT compound. The cells were frozen and sectioned, then stained using a standard IHC protocol. Mu-LUCA19 was positive on 17 out of 25 glioma-derived cell lines screened. Staining intensity ranged from ± to 3+ staining. Mu-LUCA40 was positive on 18 out of 25 glioma-derived cell lines screened. Staining intensity ranged from ± to 3+ staining. Mu-SPL-1 was positive on 14 out of 25 glioma-derived cell lines screened. Staining intensity ranged from ± to 3+ staining.

Example 7

Isolation and Characterization of Antigen Ag-SPL1, Ag-LUCA19, Ag-SG5 and Ag-LUC40

To identify the antigen to which SPL1, LUCA19, SG5 and LUCA40 were reactive, an immunoprecipitation (Ippt) experiment was performed. For immunoprecipitation, thirty 175 cm² flasks of SW480 cells were lysed with 30 ml of lysis buffer. The lysis buffer consisted of Hanks balanced salt solution (HBSS+) fortified with 2% Triton X-100, protease inhibitor cocktail (1 tablet per 5 ml lysis buffer of complete mini EDTA free protease cocktail from Roche Molecular Biochemicals), 0.1% sodium azide, and 2 mM PMSF. The cell lysate was clarified at 24,000×g for 30 minutes at 4° C. before being passed over a column consisting of 1 ml Protein G (Amersham Pharmacia). The pre-cleared SW480 lysate was then incubated with Protein G absorbed mu-SPL1, mu-LUCA19, mu-SG5 or mu-LUCA40 (10$_4$g mu-SPL1, mu-LUCA19, mu-SG5or mu-LUCA40 was pre-incubated for 30 minutes at room temp with 5 µl Protein G) for 2 hours at 4° C. The beads (both the pre-clear Protein G beads and the Protein G absorbed mu-SPL1, mu-LUCA19, mu-SG5 or mu-LUCA40 beads) were then washed three times with lysis buffer before elution with 30 µl SDS sample buffer (3% SDS, 20% Glycerol, 10 mM DTT, 2% Bromophenol blue, 0.1M Tris, pH8.0). 25 µl of the eluate was then resolved by SDS-PAGE and visualized through Coomassie staining. 5 µl of the eluate was resolved by SDS-PAGE and further transferred to nitrocellulose for western blotting.

The blot was then probed with mu-SPL1, mu-LUCA19, mu-SG5 or mu-LUCA40 and developed using a Western Blotting Kit (Invitrogen Cat. No. WB7103) to confirm antigen recognition. By western blotting the mu-SPL1, mu-LUCA19, mu-SG5 or mu-LUCA40 and mouse IgG eluate against mu-SPL1, mu-LUCA19 mu-SG5 or mu-LUCA40, a protein unique to the mu-SPL 1, mu-LUCA19, mu-SG5 or mu-LUCA40 eluate was observed. Stained protein bands from the NuPAGE gel were excised using clean scalpel blades and are placed in clean Eppendorf tubes. Excised bands were stored at −20° C. until used for protein identification by mass spectrometry.

Example 8

Characterization of the Antigen to which mu-SPL1, mu-LUCA19, mu-SG5 or mu-LUCA40 Binds Using Tandem Mass Spectrometry (MS/MS)

The antigens to which mu-SPL1, mu-LUCA19, mu-SG5 and mu-LUCA40 bind were isolated as described in Example 7 and subjected to Tandem mass spectroscopy according to the method of Kane et al. J Bio Chem. 2002 Jun. 21; 277(25): 22115-8, Epub May 06. Proteins are separated by SDS-PAGE, and the gel is stained with the colloidal Coomassie Blue reagent (Invitrogen). Proteins of interest are digested in gel with trypsin. The tryptic peptides are sequenced by microcapillary liquid chromatography MS/MS on an ion trap mass spectrometer (Thermo-Finnigan LCDQ DECA XP), as described in Wu et al., Nature 405:477-482 (2000).

Alternatively, other commonly known methods of mass spectrometry, such as MALDI mass spectrometry, are also used in the practice of this invention. The results from the mass spectroscopy analysis showed that the antigen to which mu-SPL1, mu-LUCA19, mu-SG5 and mu-LUCA40 was EphA2.

Example 9

Sandwich ELISA for Epitope Mapping of mu-SPL1, mu-LUCA19, mu-SG5 and mu-LUCA40

The specific epitope on EphA2 to which mu-SPL1, mu-LUCA19, mu-SG5 and mu-LUCA40 bind was assessed using a competitive sandwich ELISA. 50 µl/well of 10 µg/ml concentration of mu-SPL1, mu-LUCA19, mu-SG5 or mu-LUCA40 were diluted in HBSS (Hank's Balanced Salt Solution with out sodium bicarbonate and phenol red) and allowed to bind to 96-well Maxisorb micro-titer plates for 2 hours at room temperature. Coated plates are then blocked for 30 minutes with HBSS containing 1% BSA (W/V). HT-29 cells were lysed as described in example 7. The lysate is then applied to the blocked micro-titer wells at a volume of 150 µl per well. The lysates are allowed to incubate for 1 hour at room temperature. After the incubation, the plate is then washed thoroughly with blocking buffer. Biotinylated mu-SPL1, mu-LUCA19, mu-SG5 and mu-LUCA40, at a concentration of 50 µl/well, 1 µg/ml, are added into the micro-titer wells and allowed to incubate for 1 hour at room temp. Biotinylated mu-SPL1, mu-LUCA19, mu-SG5 and mu-LUCA40 were prepared by incubating 1 µl of 200 mg/ml Sulfo-NHS-LC-Biotin diluted in DMSO for every 1 mg of purified antibody for 2 hours at room temperature. The biotinylated antibodies are then quenched with a final concentration of 0.1M Tris, pH 7.4 for 30 minutes at room temperature. The biotinylated antibody is then separated from free biotin by concentrating through a 30 kDa molecular weight cut-off filter. After the 1 hour incubation of the biotinylated antibodies, the plates are washed thoroughly with HBSS. Horseradish peroxidase conjugated streptavidin (SA-HRP) is diluted into HBSS at a concentration of 1:10,000. The diluted SA-HRP is added into the washed micro-titer wells at 50 µl/well and allowed to incubate for 30 minutes at room temp. After the incubation of SA-HRP, the plate is finally washed thoroughly with HBSS and developed with the addition of 100 µl/well of 1-Step TMB substrate for a color change reaction. The development is stopped with the addition of 100 µl/well of 1M phosphoric acid diluted in Milli-Q water. The developed plate is then analyzed with a ThermoMax micro-titer plate reader at 450 nm.

From the results of the competitive sandwich ELISA, we can conclude that mu-SPL1, mu-LUCA19, mu-SG5 and mu-LUCA40 represent three antibodies binding EphA2 through two distinctive epitopes, one represented by mu-LUCA40, and the second represented by mu-SPL1. mu-LUCA19 seems to share, but not directly overlap the epitope represented by mu-SPL1. The overlap does not extend into the epitope represented by the mu-LUCA40 epitope.

Example 10

Further Characterization of mu-LUCA19 and mu-SG5

EphA2 stimulation in G55 cells, a glioma cell line that expresses endogenous EphA2, was studied using mu-LUCA19 and mu-SG5. The cells were treated with either mu-LUCA19 or mu-SG5 in increasing concentrations up to 30 µg/ml and the phosphotyrosine content of immunoprecipitated EphA2 was measured by Western blot analysis with phosphotyrosine-specific antibodies (4G10, Upstate Cell Signaling Solutions, New York). No difference in phosphotyrosine content in EphA2 immunoprecipitated from G55 cells treated with either mu-LUCA19 or mu-SG5 was seen. Control Western blots for total EphA2 content was performed to ensure that the total EphA2 protein that was immunoprecipitated was the same for each treatment condition. Similar results were seen using A549 cells and mu-LUCA19 and mu-SG5 antibodies. These results indicate that treatment of cells expressing endogenous EphA2 with either mu-LUCA19 or mu-SG5 does not increase or decrease the phosphotyrosine content of EphA2.

Example 11

Effect of mu-SPL1, mu-LUCA19 and mu-LUCA40 on Cancer Cell Lines

The ability of the antibodies to reduce cell number in vitro when grown as a monolayer can be assessed using cell monolayers grown in the presence or absence of varying amounts of test or control purified antibody and the change in cell number assessed using MTT. MTT is a dye that measures the activity of mitochondrial enzymes and correlates with relative viable cell number. Cells of interest were plated and grown in F12/DMEM (1:1) growth medium supplemented with 10% fetal bovine serum in 96 well plates. The cell lines were plated in triplicate wells of a 96-well dish at a density range of 1500-2500 cells/well. Immediately after plating, mu-SPL1, mu-LUCA19 or mu-LUCA40 was added. The cells were incubated at 37° C. in a humidified incubator at 5% CO2/air for 5 days. At the end of the assay, MTT was dissolved in PBS (5 mg/ml) and added directly to wells at 1:10 dilution. Plates were placed back in incubator for 4 hours. After the incubation, medium was removed and 100 µl DMSO was added to solubilize the MTT precipitate. Plates were read at O.D. 540 nm. In these experiments, mu-LUCA40 inhibited growth of 786-O, A549, Caki-2, ES-2, SKMES-1, and SKOV3 cell lines, and SPL1 and LUCA19 did not.

Example 12

Internalization of mu-LUCA19, mu-SG5 and mu-LUCA40 and Toxin-Conjugated Anti-Mouse IgG Mab-ZAP (Advanced Targeting Systems, San Diego, Calif.) is an anti-mouse IgG conjugated to saporin, a toxin that inhibits protein synthesis. This toxin is impermeable to the cell membrane. If a monoclonal antibody is bound to a cell-surface antigen that is internalizable, the toxin-conjugate can bind to the bound monoclonal and, thereby, be internalized and eventually kill the cell. Being dependent upon internalization for demonstration of toxic activity, the Mab-ZAP can serve to evaluate whether or not a given surface antigen will serve as a suitable target for any toxin that is dependent upon internalization to express cell toxic effects. As such, the Mab-ZAP serves as a model for such internalization-dependent toxins such as maytansinoids and calicheamicin.

For testing the internalization of mu-LUCA19 and mu-LUCA40 and saporin conjugated anti-mouse IgG by tumor cells and effect of killing the tumor cells after internalization of saporin, human glioma cells, G130 were removed from stock flasks with 10 mM EDTA and centrifuged. Cells were resuspended at 50,000/ml in appropriate medium and 100 µl plated per well in 96 well plates. Antibody mu-SPL1, mu-LUCA19 or mu-LUCA40 was added immediately to appropriate wells as a 10× concentrate, to make a final concentration of 10 ug/ml. After 15 minutes at room temperature Mab-ZAP (Cat. #IT-04, Advanced Targeting Systems, San Diego Calif.) was added to appropriate wells as 10× concentrate, to make final concentrations from 0.001 nM to 10 nM. After 4 days growth, MTT was added (stock 5 mg/ml PBS, 1:10 dilution in well) for 4 hrs at 37° C. The medium was then removed from all wells and 100 µl/well DMSO was added. The plates were gently swirled to solubilize the blue MTT precipitate and the plates were read at O.D. 540 nm.

There was a decrease in MTT staining in G130 cells in the presence of mu-LUCA19 and mu-LUCA40 as compared to staining in the absence of those antibodies. This indicates that the growth of G130 cells was inhibited in the presence of mu-LUCA19 and mu-LUCA40 and Mab-ZAP and these results are indicative of mu-LUCA19 and mu-LUCA40 and toxin-conjugated anti-mouse IgG were internalized in G130 cells. Similar results were seen using ES-2 cells, an ovarian carcinoma cell line, and mu-SG5 antibodies. There was a decrease in MTT staining in ES-2 cells in the presence of mu-SG5 as compared to staining in the absence of this antibody. This indicates that the growth of ES-2 cells was inhibited in the presence of mu-SG5 and Mab-ZAP. This result is indicative of mu-SG5 and toxin-conjugated anti-mouse IgG were internalized in ES-2cells.

Example 13

Efficacy of Anti-EphA2 Antibody SPL1 and LUCA40 with Human Cells in Nude Mice

Human tumor cells were grafted under the kidney capsule in nude (nu/nu) mice. Three tumor cell lines were used. The ES-2 and SKOV3-3 ovarian tumor-derived cell lines, and the Caki-2 kidney tumor-derived cell lines were obtained from the ATCC. In some studies both kidneys received xenografts. For the treated animals, grafts were made in the kidney capsule (500k cells in collagen gel). Anti-EphA2 monoclonal antibody SPL1 or LUCA40 was injected intraperitoneally at a concentration of 50 mg/kg and a volume of 0.01 mL/g body weight. Dosing was initiated on Day 2 following implantation, and doses of SPL1, LUCA40 or PBS were administered three times weekly as single rapid injections. Control mice were injected with PBS only. Three days after the final injection, the animals were euthanized and the kidneys with grafts were examined.

The amount of human DNA in the tumors was quantitated using real-time PCR on an Applied Biosystems (Foster City, Calif.) SDS7000 system, with primers and probe specific for the human ribosomal gene RPL19 according to published methods. Each tumor sample was analyzed in triplicate PCR reactions and average DNA concentrations were determined. Average DNA concentration and standard error of the mean was determined for each group of tumor samples. Statistical significance was determined using the Student's T-test (two-tailed, type 1). Tumor growth inhibition was calculated as the absolute value of [(average tumor volume of treated group/average tumor volume of PBS control group)×100]−100.

In data not shown, SPL1 appeared on visual and manual examination to reduce the size of tumors, relative to controls, using cell lines Caki-2 and ES-2. Similar results were seen in LUCA40 treated mice implanted with Caki-2 tumors. DNA quantitation of the Caki-2 tumors from mice treated with LUCA40 antibodies confirmed that the LUCA40 treated mice had smaller tumors relative to controls. Table 12 shows other sub-renal capsule xenograft study designs with SPL1 antibodies and DNA quantitation results from these studies.

TABLE 12

SPL1 Sub-Renal Capsule Xenograft Model Study Design and Results

| Cell Line Studied | MAb dose (mg/kg) | No. animals/group | % TGI* |
|---|---|---|---|
| ES-2 | 50 | 5 | 78.3 p = 0.006 |
| ES-2 | 50 | 6 | 61 p = 0.026 |

TABLE 12-continued

SPL1 Sub-Renal Capsule Xenograft Model Study Design and Results

| Cell Line Studied | MAb dose (mg/kg) | No. animals/group | % TGI* |
|---|---|---|---|
| SKOV3-3 | 50 | 6 | 70 p = 0.005 |

*TGI = tumor growth inhibition vs. PBS control group; p-values were determined by the Student's T-test, unpaired.

Example 14

Antitumor Efficacy of SPL1 in a Subcutaneous Model of Human Ovarian Tumors

This study was designed to test the dose-responsive antitumor data for SPL1 antibody in a subcutaneous model of ovarian cancer and lung cancer.

The ES-2 ovarian tumor-derived cell line was re-derived from a rapid-growing tumor identified in a pilot subcutaneous tumor model study. A549 lung tumor-derived cells were obtained from the ATCC. Cultured cells were trypsinized, washed in media, spun down and resuspended in media at 100 million cells per milliliter of media (5 million cells per 0.05 mL volume), then mixed in an equal volume of Matrigel® for a final injection volume of 0.1 mL. Female CRL. nu/nu homozygous mice were used. Cells were inoculated by subcutaneous injection in the back of the neck of the mice. Dosing was initiated either on the day of implantation or when tumors were established and measurable. For Day 0 dosing, tumors were implanted in the morning and animals dosed in the afternoon of the same day. For established tumors, animals were randomized among groups as follows: tumor volumes were determined, animals were sorted by tumor volume, the mean was determined and the appropriate number of animals (12 to 15 per group depending on the model) was selected above and below the mean, removing from the study those with small or large tumors. The remaining animals were randomized by ear tag number into treatment and control groups. The random distribution of the final groups was confirmed by T-test (p>0.1 was considered randomized).

For each treatment dose group, SPL1 was diluted in PBS at an appropriate concentration dose (50 mg/kg for ES2 cells study and a concentration range of 10mg/kg, 30 mg/kg and 100 mg/kg for A549 cells study) and PBS control and administered at a volume of 0.01 mL/g body weight. Doses of SPL1 or PBS were administered twice weekly as single rapid injections into the intraperitoneal cavity. Control mice were injected with PBS only. Dosing was initiated in groups of 12-15 mice when tumors reached the appropriate size, depending on the study.

Tumors were allowed to grow for approximately 6 days prior to initial tumor measurement. Tumors were subsequently measured twice weekly by digital caliper in three dimensions, and tumor volume was calculated as one-half the product of the three measurements. Tumor volume over time was the primary endpoint for all studies. Clinical observations were made daily. Body weight was determined for each animal twice weekly.

Average tumor volumes and standard error of the mean were determined for each group at each measurement. Statistical significance was determined using the Student's T-test (two-tailed, type 1). Tumor growth inhibition was calculated as the absolute value of [(average tumor volume of treated group/average tumor volume of PBS control group)×100]−100. Table 13 shows subcutaneous xenograft study designs and results.

TABLE 13

SPL1 SC Xenograft Model Study Design and Results

| Cell Line Studied | MAb dose (mg/kg) | Dose Regimen | No. animals/group | % TGI* |
|---|---|---|---|---|
| ES-2 | 50 | Start dosing Day 0 | 12 | 44.9% p = 0.045 Day 18 |
| | PBS | Start dosing Day 0 | 12 | NA |
| | 50 | Start dosing when tumors reach 100-150 mm³ | 12-15 | 47.6% p = 0.012 Day 21 |
| | PBS | Start dosing when tumors reach 100-200 m³ | 12-15 | NA |
| A549 | 10 | Start dosing when tumors reach 100 mm³ | 15 | 67.5% p = <0.001 Day 34 |
| | 30 | Start dosing when tumors reach 100 mm³ | 15 | 82.2% p = <0.001 Day 34 |
| | 100 | Start dosing when tumors reach 100 mm³ | 15 | 80.4% p = <0.001 Day 34 |
| | PBS | Start dosing when tumors reach 100 mm³ | 15 | NA |

*TGI = tumor growth inhibition vs. PBS control group.

As shown in FIG. 1, a subset of SPL1 treated A549 tumor xenografts was found to re-grow slowly after cessation of dosing, with tumor re-growth defined as an increase in volume of two-fold or more after cessation of dosing. 7 out of 16 mice in the 100 mg/kg treatment group had tumor regrowth, while 9 out of 16 mice in the 100 mg/kg treatment group remained tumor free after cessation of dosing. Similarly, 3 out of 15 mice in the 30 mg/kg treatment group had tumor regrowth, while 12/15 mice in the 30 mg/kg remained tumor free after cessation of dosing. The graphed results in FIG. 1 after the "stop dosing" point represent only the tumor size from mice that had tumor regrowth.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

We claim:

1. An isolated nucleic acid sequence that encodes an EphA2 antibody, wherein said antibody specifically binds to EphA2 and comprises the three complementarity determining regions from the heavy chain and the three complementarity determining regions from the light chain of antibody LUCA19 produced by the cell line having ATCC No. PTA-5070.

2. The nucleic acid of claim 1, wherein the nucleic acid is operably linked to a promoter.

3. The nucleic acid of claim 2, wherein the promoter and the nucleic acid are contained in an expression vector.

4. The nucleic acid of claim 1, wherein said EphA2 antibody is an antigen-binding fragment selected from the group consisting of a Fab, a Fab', a F(ab')$_2$ and a Fv; wherein said antigen binding fragment retains the binding specificity of antibody LUCA19 produced by the cell line having ATCC No. 5070.

5. A cell line transfected, transformed, or infected with a vector containing a nucleic acid of claim 1.

6. A method for producing a substantially purified immunoglobulin, or an antigen binding fragment thereof, comprising the steps of:
   a. Growing a cell line transformed with the nucleic acid of claim 1 under conditions in which the immunoglobulin or antigen binding fragment is expressed; and
   b. Harvesting the expressed immunoglobulin or fragment.

7. The method of claim 6, wherein the cell line is a hybridoma.

8. The nucleic acid of claim 1, wherein said EphA2 antibody is a humanized antibody.

9. The nucleic acid of claim 8, wherein said EphA2 antibody is an antigen-binding fragment selected from the group consisting of a Fab, a Fab', a F(ab')$_2$ and a Fv; wherein said antigen binding fragment retains the binding specificity of antibody LUCA19 produced by the cell line having ATCC No. 5070.

10. An isolated nucleic acid sequence that encodes an EphA2 antibody, wherein said antibody specifically binds to EphA2 and comprises the three complementarity determining regions from the heavy chain and the three complementarity determining regions from the light chain of antibody SPL1 produced by the cell line having ATCC No. PTA-6059.

11. The nucleic acid of claim 10, wherein the nucleic acid is operably linked to a promoter.

12. The nucleic acid of claim 11, wherein the promoter and the nucleic acid are contained in an expression vector.

13. The nucleic acid of claim 10, wherein said EphA2 antibody is an antigen-binding fragment selected from the group consisting of a Fab, a Fab', a F(ab')$_2$ and a Fv; wherein said antigen binding fragment retains the binding specificity of antibody SPL1 produced by the cell line having ATCC No. 6059.

14. A cell line transfected, transformed, or infected with a vector containing a nucleic acid of claim 10.

15. A method for producing a substantially purified immunoglobulin, or an antigen binding fragment thereof, comprising the steps of:
   a. Growing a cell line transformed with the nucleic acid of claim 10 under conditions in which the immunoglobulin or antigen binding fragment is expressed; and
   b. Harvesting the expressed immunoglobulin or fragment.

16. The method of claim 15, wherein the cell line is a hybridoma.

17. The nucleic acid of claim 10, wherein said EphA2 antibody is a humanized antibody.

18. The nucleic acid of claim 17, wherein said EphA2 antibody is an antigen-binding fragment selected from the group consisting of a Fab, a Fab', a F(ab')$_2$ and a Fv; wherein said antigen binding fragment retains the binding specificity of antibody SPL1 produced by the cell line having ATCC No. 6059.

19. An isolated nucleic acid sequence that encodes an EphA2 antibody, wherein said antibody specifically binds to EphA2 and comprises the three complementarity determining regions from the heavy chain and the three complementarity determining regions from the light chain of antibody LUCA40 produced by the cell line having ATCC No. PTA-6056.

20. The nucleic acid of claim 19, wherein the nucleic acid is operably linked to a promoter.

21. The nucleic acid of claim 20, wherein the promoter and the nucleic acid are contained in an expression vector.

22. The nucleic acid of claim 19, wherein said EphA2 antibody is an antigen-binding fragment selected from the group consisting of a Fab, a Fab', a F(ab')$_2$ and a Fv; wherein said antigen binding fragment retains the binding specificity of antibody LUCA40 produced by the cell line having ATCC No. 6056.

23. A cell line transfected, transformed, or infected with a vector containing a nucleic acid of claim 19.

24. A method for producing a substantially purified immunoglobulin, or an antigen binding fragment thereof, comprising the steps of:
   a. Growing a cell line transformed with the nucleic acid of claim 10 under conditions in which the immunoglobulin or antigen binding fragment is expressed; and
   b. Harvesting the expressed immunoglobulin or fragment.

25. The method of claim 24, wherein the cell line is a hybridoma.

26. The nucleic acid of claim 19, wherein said EphA2 antibody is a humanized antibody.

27. The nucleic acid of claim 26, wherein said EphA2 antibody is an antigen-binding fragment selected from the group consisting of a Fab, a Fab', a F(ab')$_2$ and a Fv; wherein said antigen binding fragment retains the binding specificity of antibody LUCA40 produced by the cell line having ATCC No. 6056.

28. An isolated nucleic acid sequence that encodes an EphA2 antibody, wherein said antibody specifically binds to EphA2 and comprises the three complementarity determining regions from the heavy chain and the three complementarity determining regions from the light chain of antibody SG5 produced by the cell line having ATCC No. PTA-7356.

29. The nucleic acid of claim 28, wherein the nucleic acid is operably linked to a promoter.

30. The nucleic acid of claim 29, wherein the promoter and the nucleic acid are contained in an expression vector.

31. The nucleic acid of claim 28, wherein said EphA2 antibody is an antigen-binding fragment selected from the group consisting of a Fab, a Fab', a F(ab')$_2$ and a Fv; wherein said antigen binding fragment retains the binding specificity of antibody LUCA19 produced by the cell line having ATCC No. 5070.

32. A cell line transfected, transformed, or infected with a vector containing a nucleic acid of claim 28.

33. A method for producing a substantially purified immunoglobulin, or an antigen binding fragment thereof, comprising the steps of:
   a. Growing a cell line transformed with the nucleic acid of claim 28 under conditions in which the immunoglobulin or antigen binding fragment is expressed; and
   b. Harvesting the expressed immunoglobulin or fragment.

34. The method of claim 33, wherein the cell line is a hybridoma.

35. The nucleic acid of claim 28, wherein said EphA2 antibody is a humanized antibody.

36. The nucleic acid of claim 35, wherein said EphA2 antibody is an antigen-binding fragment selected from the group consisting of a Fab, a Fab', a F(ab')$_2$ and a Fv; wherein said antigen binding fragment retains the binding specificity of antibody SG5 produced by the cell line having ATCC No. 7356.

* * * * *